[19] United States Patent
Smith et al.

[11] Patent Number: 5,880,901
[45] Date of Patent: Mar. 9, 1999

[54] METHOD AND APPARATUS FOR POSITIONING A MAGNETORESISTIVE HEAD

[75] Inventors: Gordon J. Smith; Hal Hjalmar Ottesen, both of Rochester, Minn.

[73] Assignee: International Business Machines Corporation, Armonk, N.Y.

[21] Appl. No.: 888,879

[22] Filed: Jul. 7, 1997

Related U.S. Application Data

[62] Division of Ser. No. 581,981, Jan. 2, 1996, Pat. No. 5,739,972.

[51] Int. Cl.$^6$ ................................................... G11B 21/02
[52] U.S. Cl. .......................... 360/75; 360/25; 360/77.04
[58] Field of Search .................................. 360/77.03, 75, 360/25, 77.04; 374/113, 141

[56] References Cited

U.S. PATENT DOCUMENTS

| | | |
|---|---|---|
| 3,416,373 | 12/1968 | Havens . |
| 3,918,091 | 11/1975 | Walraven et al. .................... 360/109 X |
| 4,430,010 | 2/1984 | Zrenner et al. ........................... 374/45 |
| 4,485,337 | 11/1984 | Sandusky ................................. 318/314 |
| 4,498,146 | 2/1985 | Martinez ................................. 364/900 |
| 4,532,802 | 8/1985 | Yeack-Scranton et al. .......... 73/432 R |
| 4,647,992 | 3/1987 | Vinal ................................. 360/113 X |
| 4,669,011 | 5/1987 | Lemke ..................................... 360/103 |
| 4,691,259 | 9/1987 | Imakoshi et al. ........................ 360/113 |
| 4,712,144 | 12/1987 | Klaassen ..................................... 360/67 |
| 4,747,698 | 5/1988 | Wickramsinghe et al. ................. 374/6 |
| 4,762,427 | 8/1988 | Hori et al. ............................... 374/141 |
| 4,777,544 | 10/1988 | Brown et al. ............................. 360/75 |
| 4,802,033 | 1/1989 | Chi ...................................... 360/77.04 |
| 4,853,810 | 8/1989 | Pohl et al. ............................... 360/103 |

(List continued on next page.)

FOREIGN PATENT DOCUMENTS

| | | |
|---|---|---|
| 0 242 597 | 10/1987 | European Pat. Off. . |
| 61-177622 | 8/1986 | Japan . |
| 63-191316 | 8/1988 | Japan . |
| 1-98180 | 4/1989 | Japan . |
| 4-95218 | 3/1992 | Japan . |
| 4-109421 | 4/1992 | Japan . |
| 4-141822 | 5/1992 | Japan . |
| 5-174515 | 7/1993 | Japan . |
| 06290563 | 10/1994 | Japan . |

OTHER PUBLICATIONS

S.Z. Dushkes and R. J. Surty, "Head Crash Detector", May 1971, IBM Technical Disclosure Bulletin, vol. 13, No. 12, p. 3685.

L. R. Bellamy and J. D. Luciani, "Disk Drive Motor Speed Control", Apr. 1981, IBM Technical Disclosure Bulletin, vol. 23. No. 11, p. 5163.

E. G. Gruss and A. R. Tietze, "Servo System For Magnetic Recording Based On Time Comparison", Jul. 1980, IBM Technical Disclosure Bulletin vol. 23, No. 2, pp. 787–789.

R. E. Fontana, Jr., D. E. Horne and H. Sussner, "Disk Asperity Detector", Aug. 1883, IBM Technical Disclosure Bulletin, vol. 26, No. 3A, pp. 1278–1280.

G. J. Kerwin, J. M. Poss and D. P. Swart, "Fast Offset Recovery For Thermal Asperity Data Recovery Procedure", Apr. 1992, IBM Technical Disclosure Bulletin, vol. 34, No. 11, pp. 217–219.

(List continued on next page.)

Primary Examiner—Andrew L. Sniezek
Attorney, Agent, or Firm—Merchant Gould Smith Edell Welter & Schmidt; Matthew J. Bussan

[57] ABSTRACT

The present invention is a method and apparatus for positioning a magnetoresistive (MR) head relative to a storage medium in a storage device. The storage medium is mounted in the storage device to allow relative movement between the MR head and the storage medium. The storage medium includes servo information provided to induce a thermal response in the MR head. A controller controls the relative movement between the MR head and the storage medium using the thermal response induced in the MR head.

7 Claims, 32 Drawing Sheets

U.S. PATENT DOCUMENTS

| | | | |
|---|---|---|---|
| 4,914,398 | 4/1990 | Jove et al. | 328/167 |
| 4,931,887 | 6/1990 | Hegde et al. | 360/75 |
| 4,949,036 | 8/1990 | Bezinque et al. | 342/212 |
| 5,032,935 | 7/1991 | Jove et al. | 360/67 |
| 5,054,936 | 10/1991 | Fraden | 374/164 |
| 5,057,785 | 10/1991 | Chung et al. | 328/162 |
| 5,070,495 | 12/1991 | Bletscher, Jr. et al. | 369/116 |
| 5,079,663 | 1/1992 | Ju et al. | 360/113 |
| 5,084,791 | 1/1992 | Thanos et al. | 360/77.04 |
| 5,130,866 | 7/1992 | Klaassen et al. | 360/75 |
| 5,168,413 | 12/1992 | Coker et al. | 360/137 |
| 5,185,681 | 2/1993 | Volz et al. | 360/77.05 |
| 5,212,677 | 5/1993 | Shimote et al. | 369/58 |
| 5,233,482 | 8/1993 | Galbraith et al. | 360/46 |
| 5,301,080 | 4/1994 | Ottesen et al. | 300/113 |
| 5,321,559 | 6/1994 | Nguyen et al. | 360/46 |
| 5,327,298 | 7/1994 | Ottesen et al. | 360/48 |
| 5,345,342 | 9/1994 | Abbott et al. | 360/48 |
| 5,367,409 | 11/1994 | Ottesen et al. | 360/32 |
| 5,377,058 | 12/1994 | Good et al. | 360/75 |
| 5,388,014 | 2/1995 | Brug et al. | 360/66 |
| 5,402,278 | 3/1995 | Morita | 360/77.05 |
| 5,418,770 | 5/1995 | Ide et al. | 369/116 |
| 5,424,885 | 6/1995 | McKenzie et al. | 360/77.05 |
| 5,430,706 | 7/1995 | Utsunomiya et al. | 369/275.1 |
| 5,455,730 | 10/1995 | Dovek et al. | 360/113 |
| 5,457,585 | 10/1995 | Christensen | 360/75 |
| 5,527,110 | 6/1996 | Abraham et al. | 374/5 |

OTHER PUBLICATIONS

K. B. Klaassen, "Magnetic Recording Channel Front–Ends", Nov. 1, 1991, IBM Research Report, pp. 1–6.

Research Disclosure, "Asperity Knee Detection Using Harmonic Ratio Flyheight", Mar. 1991, Emsworth Design, Inc., No. 323, p. 190.

Chau Lin, "Techniques For The Measurement Of Air–Bearing Separation–A Review", Dec. 1973, IEEE Transactions on Magnetics, vol. MAG–9, No. 4, pp. 673–677.

F. W. Gorter et al., "Magnetoresistive Reading Of Information", Sep. 1974, IEEE Transactions on Magnetics, vol. MAG–10, No. 3, pp. 899–902.

F. E. Talke et al., "Surface Defect Studies Of Flexible Media Using Magnetoresistive Sensors", Sep. 1975, IEEE Tansactions on Magnetic, vol. MAG–11, No. 5, pp. 1188–1190.

Shoji Tanaka, et al., "Characterization Of Magnetizing Process for Pre–Embossed Servo Pattern Of Plastic Hard Disks", Mar. 1994, IEEE Transactions on Magnetics, vol. 30, No. 2, pp. 4210–4211.

Hiroaki Yada et al., "High Areal Density Recording Using An MR/Inductive Head And Pre–Embossed Rigid Magnetic Disk", Mar. 1994, IEEE Tansactions on Magnetics, vol. 30, No. 2, pp. 404–409.

Y. Li et al., "The Determination Of Flash Temperature In Intermittent Magnetic Head/Disk Contacts Using Magnetoresistive Heads", Jan. 1993, Journal of Tribology, vol. 115, No. 1, pp. 179–184.

Shoji Tanaka et al., "Characterization Of Magnetizing Process For Pre–Embossed Servo Pattern Of Plastic Hard Disks", Nov. 1994, IEEE Transactions on Magnetics, vol. 30, No. 6, pp. 4209–4211.

Kenjiro Watanabe et al., "Demonstration Of Track Following Technique Based On Discrete Track Media", Nov. 1993, IEEE Transactions on Magnetics, vol. 29, No. 6, p. 4030–4032.

K. Watanbe et al., Demonstration Of Track Following Technic Based On Discrete Track Media, pp. 1–3.

Osamu Morita et al., "Magnetization Characteristics Of Pre–Embossed Patterns On The Molded Plastic Rigid Disk".

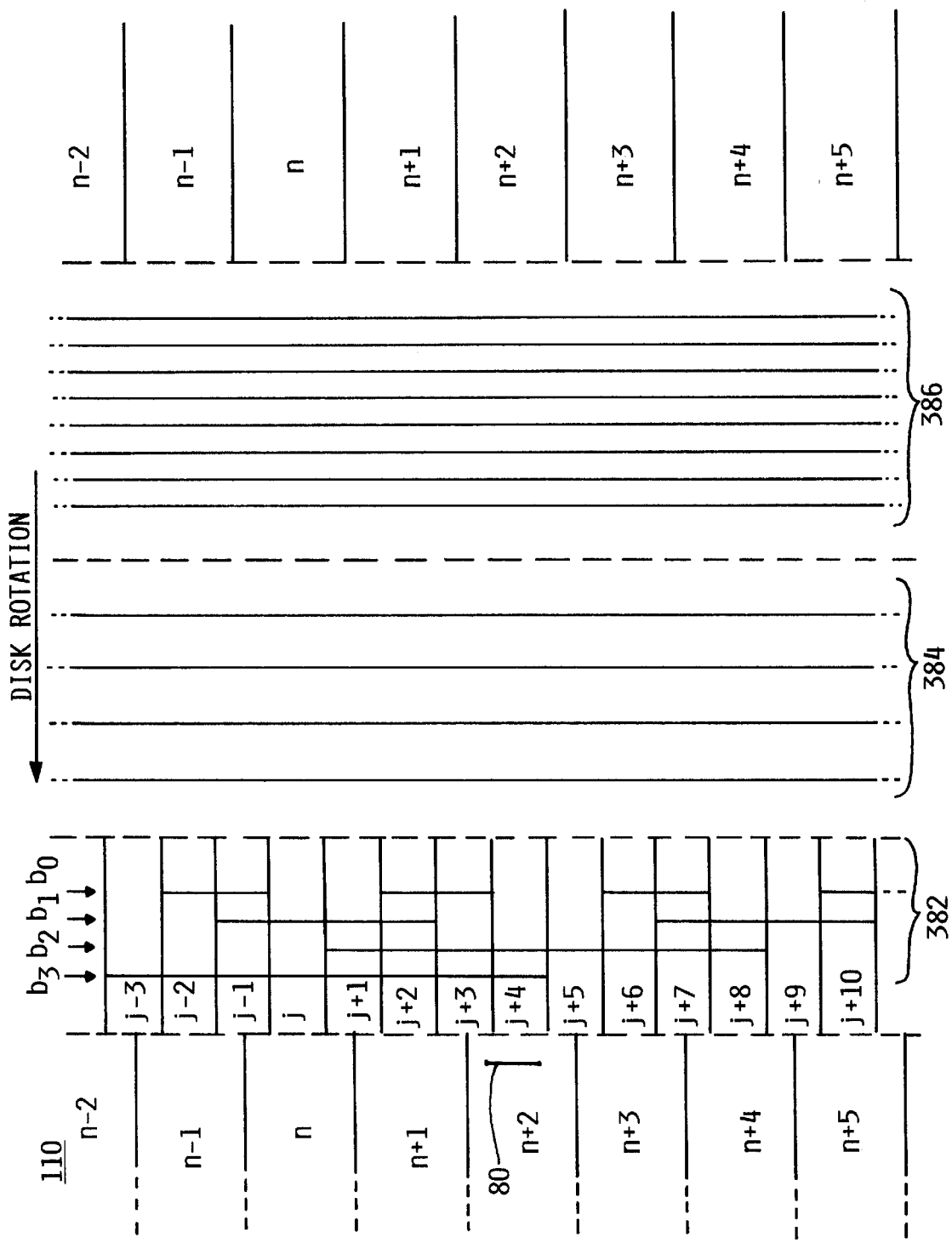

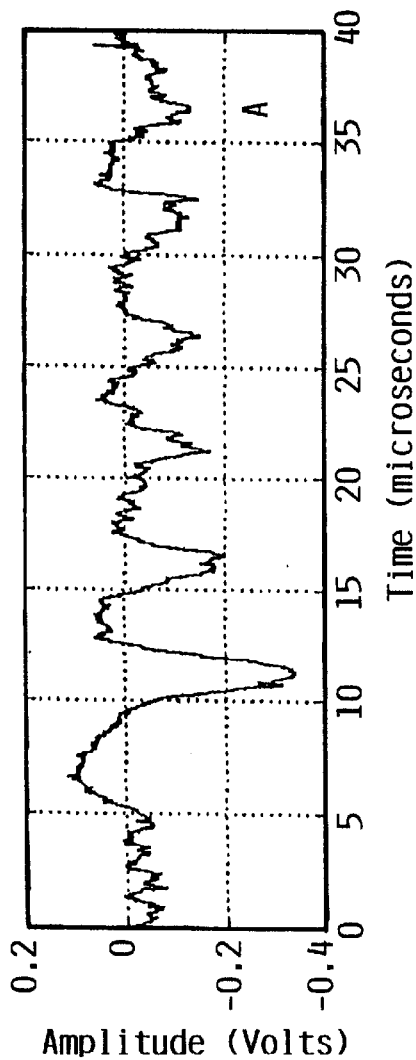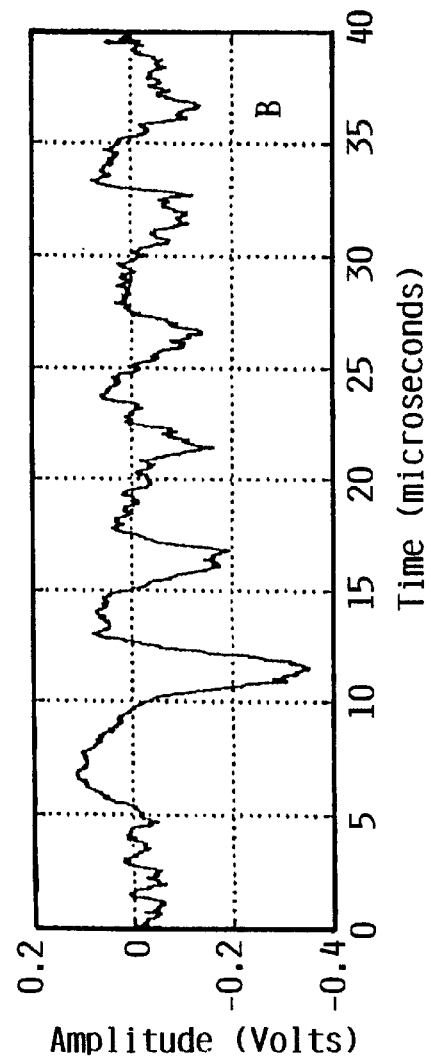
FIG. 17A
FIG. 17B

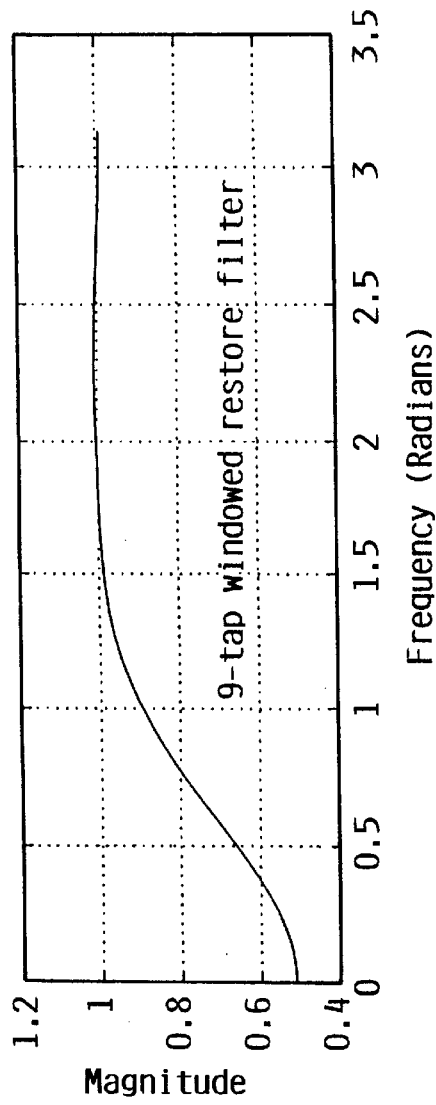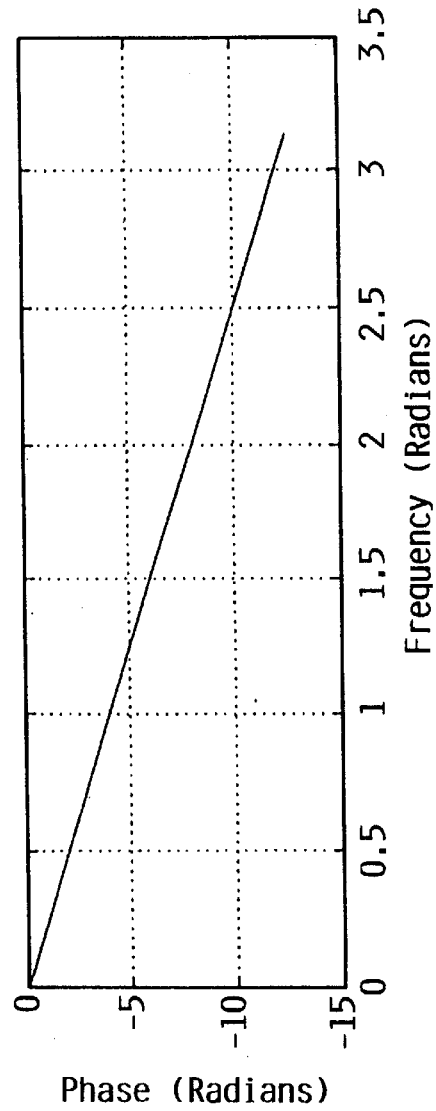

METHOD AND APPARATUS FOR POSITIONING A MAGNETORESISTIVE HEAD

This is a Divisional of application Ser. No. 08/581,981, filed Jan. 2, 1996, now U.S. Pat. No. 5,739,972 which applications are incorporated herein by reference.

FIELD OF THE INVENTION

The present invention relates generally to data storage systems, and, more particularly, to a method and apparatus for positioning a magnetoresistive head relative to a storage medium.

BACKGROUND OF THE INVENTION

A typical data storage system includes a magnetic medium for storing data in magnetic form and a transducer used to read and/or write magnetic data from/to the storage medium. A disk storage device, for example, includes one or more data storage disks coaxially mounted on a hub of a spindle motor. The spindle motor rotates the disks at speeds typically on the order of several thousand revolutions-per-minute. Digital information, representing various types of data, is typically written to and read from the data storage disks by one or more transducers, or read/write heads, which are mounted to an actuator assembly and passed over the surface of the rapidly rotating disks.

The actuator assembly typically includes a coil assembly and a plurality of outwardly extending arms having flexible suspensions with one or more transducers and slider bodies being mounted on the suspensions. The suspensions are interleaved within the stack of rotating disks, typically by means of an arm assembly (E/block) mounted to the actuator assembly. The coil assembly generally interacts with a permanent magnet structure, and is responsive to a controller. A voice coil motor (VCM) is also mounted to the actuator assembly diametrically opposite the actuator arms.

In a typical digital data storage system, digital data is stored in the form of magnetic transitions on a series of concentric, spaced tracks comprising the surface of the magnetizable rigid data storage disks. The tracks are generally divided into a plurality of sectors, with each sector comprising a number of information fields. One of the information fields is typically designated for storing data, while other fields contain track and sector position identifications and synchronization information, for example. Data is transferred to, and retrieved from, specified track and sector locations by the transducers which follow a given track and move from track to track, typically under the servo control of a controller.

The head slider body is typically designed as an aerodynamic lifting body that lifts the MR head off the surface of the disk as the rate of spindle motor rotation increases, and causes the MR head to hover above the disk on an air-bearing cushion produced by high speed disk rotation. The separation distance between the MR head and the disk, typically 0.1 microns or less, is commonly referred to as head-to-disk spacing.

Writing data to a data storage disk generally involves passing a current through the write element of the transducer assembly to produce magnetic lines of flux which magnetize a specific location of the disk surface. Reading data from a specified disk location is typically accomplished by a read element of the transducer assembly sensing the magnetic field or flux lines emanating from the magnetized locations of the disk. As the read element passes over the rotating disk surface, the interaction between the read element and the magnetized locations on the disk surface results in the production of electrical signals in the read element. The electrical signals correspond to transitions in the magnetic field.

Conventional data storage systems generally employ a closed-loop servo control system for positioning the actuator and read/write transducers to specified storage locations on the data storage disk. During normal data storage system operation, a servo transducer, generally mounted proximate the read/write transducers, or, alternatively, incorporated as the read element of the transducer, is typically employed to read information for the purpose of following a specified track (track following) and seeking specified track and data sector locations on the disk (track seeking).

A servo writing procedure is typically implemented to initially record servo pattern information on the surface of one or more of the data storage disks. A servo writer assembly is typically used by manufacturers of data storage systems to facilitate the transfer of servo pattern data to one or more data storage disks during the manufacturing process.

In accordance with one known servo technique, embedded servo pattern information is written to the disk along segments extending in a direction generally outward from the center of the disk. The embedded servo pattern is thus formed between the data storing sectors of each track. It is noted that a servo sector typically contains a pattern of data, often termed a servo burst pattern, used to maintain optimum alignment of the read/write transducers over the centerline of a track when reading and writing data to specified data sectors on the track. The servo information may also include sector and track identification codes which are used to identify the position of the transducer. Embedded servo offers significantly higher track densities than dedicated servo since servo information is co-located with the targeted data information (and servo information may be taken from one, single disk surface).

In a further effort to increase disk capacity, a proposed servo information format was developed, termed pre-embossed rigid magnetic (PERM) disk technology. As described and illustrated in Tanaka et al., Characterization of Magnetizing Process for Pre-Embossed Servo Pattern of Plastic Hard Disks, I.E.E.E. Transactions on Magnetics 4209 (Vol. 30, No. 2, November 1994), a PERM disk contains servo information in a number of servo zones spaced radially about the disk. Each servo zone contains pre-embossed recesses and raised portions to form a fine pattern, clock mark, and address code. The fine pattern and address code are used to generate servo information signals. To generate the servo signals, the magnetization direction of the raised portions and the recesses must be opposite. The magnetization process involves first magnetizing the entire disk in one direction using a high-field magnet. Then, a conventional write head is used to magnetize the raised areas in the opposite direction.

While use of a PERM disk may increase disk capacity, such an approach suffers from a number of shortcomings. Servo information is provided on a PERM servo disk in a two-step magnetization process, as described above. This significantly increases the amount of time required to write servo information to the disk. Moreover, during the second step of the process, servo information is not yet available on the disk. Thus, an external positioning system must be employed, thereby increasing the cost of the servo writing process. Additional concerns associated with PERM disk technology include durability.

Finally, the PERM disk, like other embedded servo techniques, still stores servo information in disk space which could otherwise be used for data storage. As a result, PERM disk technology, although still at the research level, has not been widely accepted by industry.

There exists in the data storage system manufacturing industry a need for a servo information format which is inexpensive to provide and which optimizes the data capacity of a disk. The present invention addresses these and other needs.

SUMMARY OF THE INVENTION

The present invention is a method and apparatus for positioning a magnetoresistive (MR) head relative to a storage medium in a storage device. The storage medium is mounted in the storage device to allow relative movement between the MR head and the storage medium. The storage medium includes servo information provided to induce a thermal response in the MR head. A controller controls the relative movement between the MR head and the storage medium using the thermal response induced in the MR head.

BRIEF DESCRIPTION OF THE DRAWINGS

FIG. 11(a) is a view of a segment of a calibration zone in accordance with the present invention.

FIG. 17(a) is a showing of a thermal signal extracted from a readback signal induced in an MR head at a particular track location, and FIG. 17(b) is a readback signal obtained from the same track location after AC erasure;

DETAILED DESCRIPTION OF THE EMBODIMENTS

Figure 1:
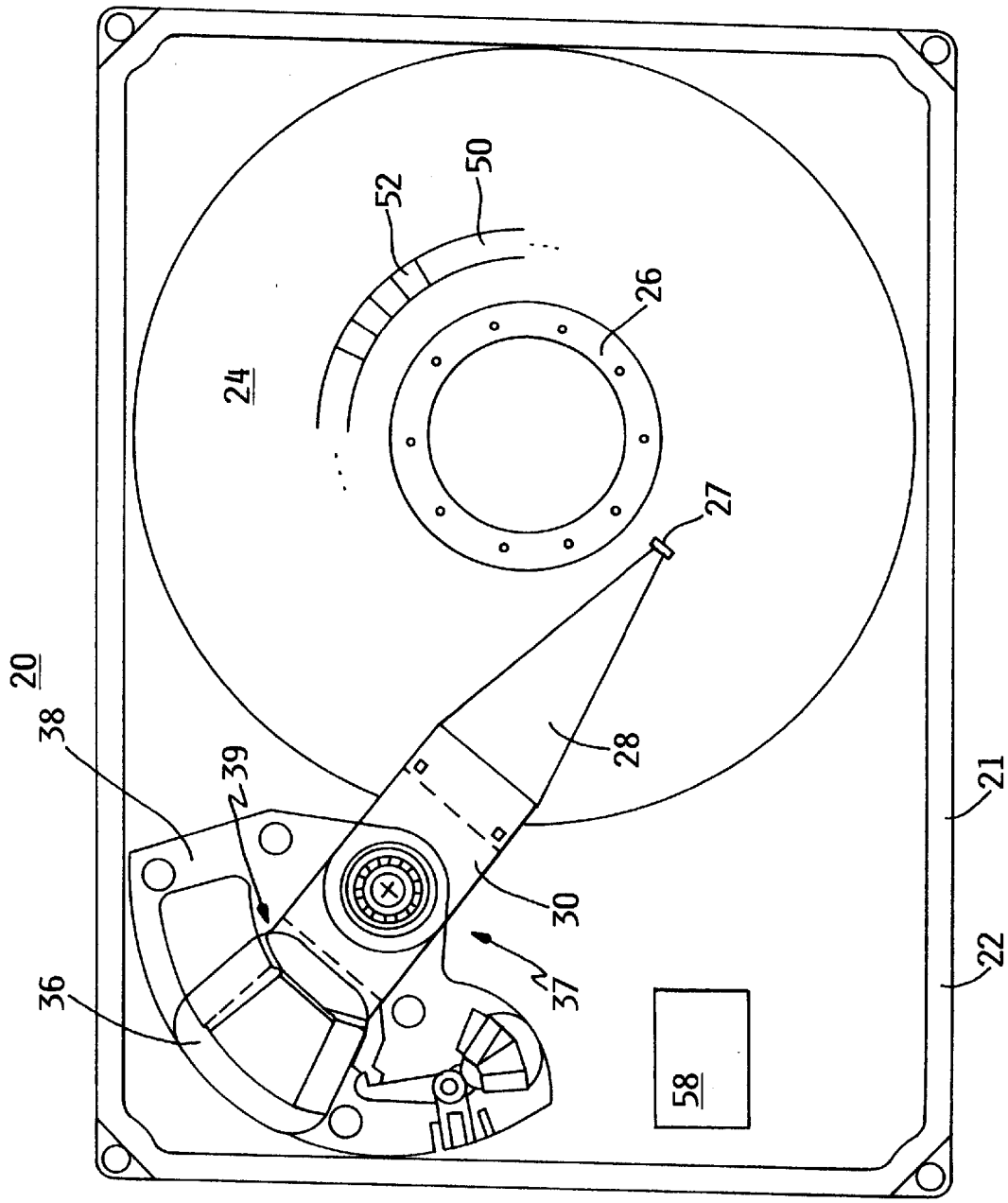
FIG. 1 is a top view of a data storage system with its upper housing cover removed.
Figure 2:
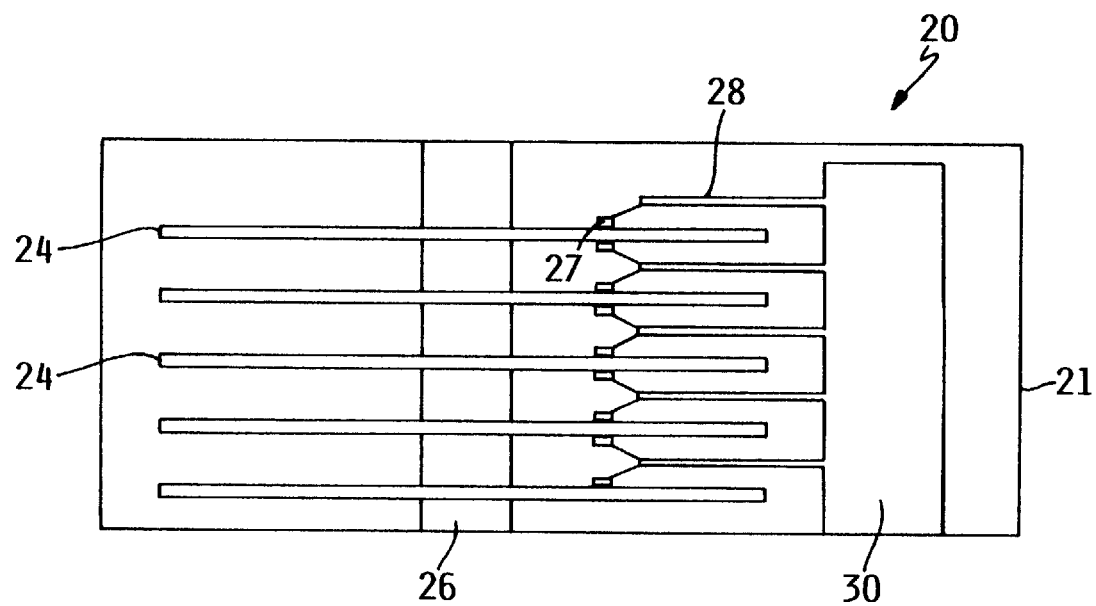
FIG. 2 is a side plan view of a data storage system comprising a plurality of data storage disks.

Referring now to the drawings, and more particularly to FIGS. 1 and 2, there is shown a data storage system 20 with its cover (not shown) removed from the base 22 of the housing 21. The data storage system 20 typically includes one or more rigid data storage disks 24 which rotate about a spindle motor 26. An actuator assembly 37 typically includes a plurality of interleaved actuator arms 30, with each arm having one or more suspensions 28 and transducers 27. The transducers 27 typically include a magnetoresistive (MR) element for reading and writing information to and from the data storage disks 24. The transducer 27 may be, for example, an MR head having a write element and a MR read element. The actuator assembly 37 includes a coil assembly 36 which cooperates with a permanent magnet structure 38 to operate as an actuator voice coil motor (VCM) 39 responsive to control signals produced by a controller 58. The controller 58 preferably includes control circuity that coordinates the transfer of data to and from the data storage disks 24, and cooperates with the VCM 39 to move the actuator arms 30, suspensions 28, and transducers 27 to prescribed track 50 and sector 52 locations when reading and writing data to and from the disks 24.

Figure 3:
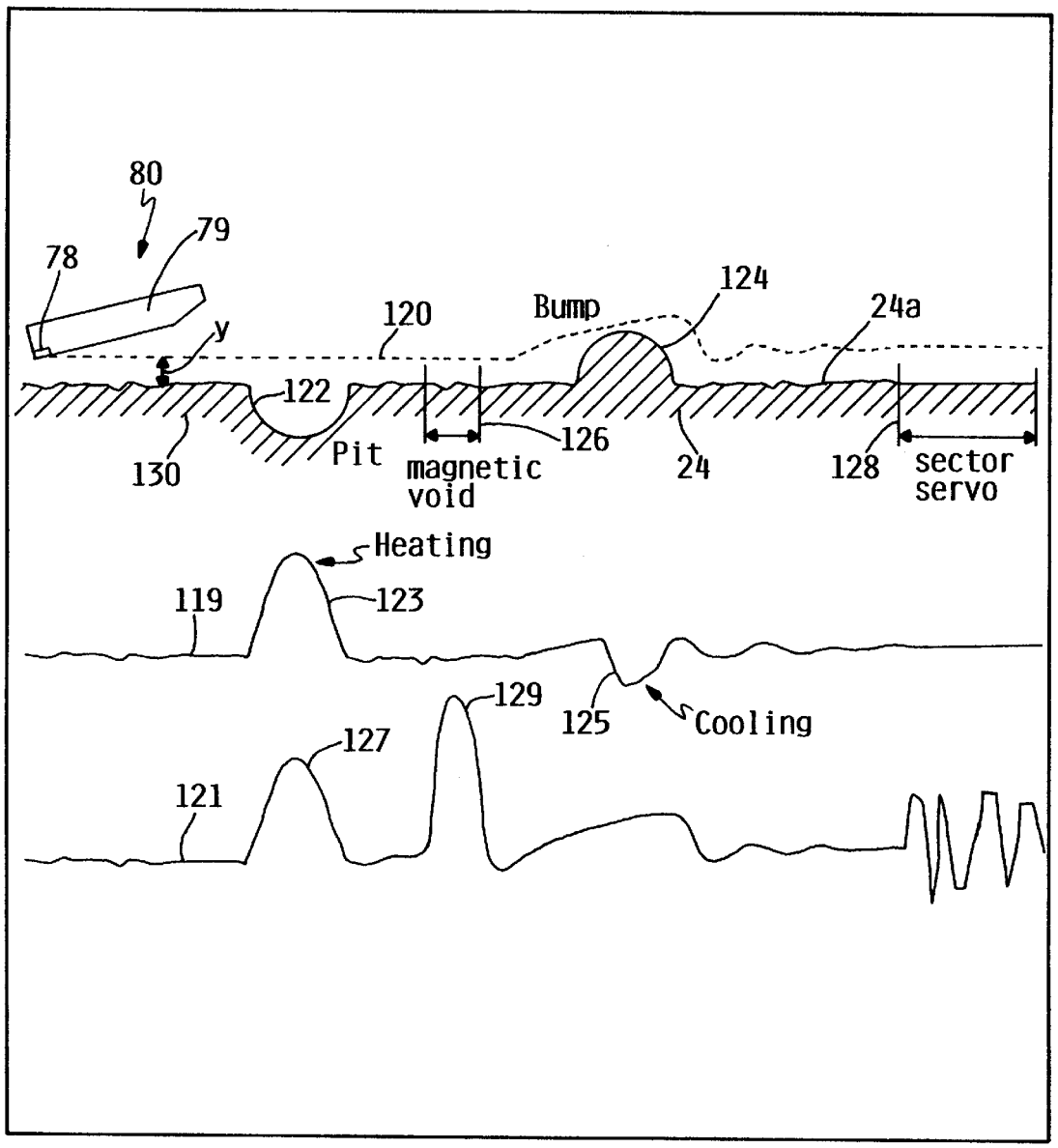
FIG. 3 is an exaggerated side view showing a data storage disk exhibiting various surface defects and features, and a thermal and magnetic response of an MR head to such defects and features.

In FIG. 3, there is illustrated an exaggerated side plan view of an MR head slider 79 flying in proximity with the surface 24a of a magnetic data storage disk 24. The disk surface 24a has a generally varying topography at the microscopic level, and often includes various surface defects, such as a pit 122, a bump 124, or a surface portion 126 void of magnetic material. It has been determined by the inventors that the thermal response of an MR head 80 changes as a function of the spacing, denoted by the parameter y, between an MR element 78 of the MR head 80 and the disk surface 24a. Head-to-disk spacing changes result in concomitant changes in heat transfer between the MR element 78 and disk 24. This heat transfer results in an alteration in the temperature of the MR element 78. Temperature changes the MR element 78 result in corresponding changes in the electrical resistance of the MR element 78 and, therefore, the output voltage of the MR element 78.

As the instantaneous head-to-disk spacing (y) increases, there results a corresponding increase in air space insulation between the MR head 80 and the disk surface 24a, thereby causing an increase in the temperature of the MR element 78. This temperature increase in the MR element 78 results in a corresponding increase in the MR head 80 resistance due to the positive temperature coefficient of the MR element material typically used to fabricate the MR element 78. Permalloy, for example, is a preferred material used to fabricate the MR element 78 and demonstrates a temperature coefficient of $+3 \times 10^{-3}/°$ C. An MR head 80 passing over a bump 124 on the disk surface 24a, by way of example, results in increased heat transfer occurring between the MR element 78 and the disk surface 24a, thereby causing cooling of the MR element 78. Such cooling of the MR element 78 causes a decrease in the MR element 78 resistance which, in turn, results in a corresponding decrease in the voltage $V_{TH}$ across the MR element 78 at a constant bias current.

It can be seen by referring to the pit 122 depicted on the disk surface 24a that the thermal voltage signal $V_{TH}$ 119 across the MR element 78 increases in amplitude as a function of increasing head-to-disk separation distance (y). It can further be seen by referring to the bump 124 depicted on the disk surface 24a that the thermal voltage signal $V_{TH}$ 119 decreases in amplitude as a function of decreasing head-to-disk separation distance. The thermal signal component of the readback signal, therefore, is in fact an information signal that can be used to detect the presence and relative magnitude of topographical variations in the surface of a magnetic data storage disk 24.

Also shown in FIG. 3 is a magnetic spacing signal 121 which has been conditioned to correspond to variations in the disk surface 24a. It can be seen that the magnetic spacing signal 121 incorrectly indicates the presence of some surface features, such as magnetic voids 126, as variations in the topography of the disk surface 24a. It can further be seen that the magnetic spacing signal 121 provides an inferior indication of other surface features, such as bumps, when compared to disk surface imaging information provided by use of the thermal signal 119.

As described more fully below, the thermal component of an MR element readback signal may be extracted to obtain information regarding surface characteristics of the rotating disk 24. In accordance with an exemplary embodiment of the invention, servo information is encoded in a surface profile of the disk 24 and is read using a transducer having an MR element, e.g., an MR head 80. As will be appreciated from the exemplary embodiments described below, because the servo information is provided in the profile of the disk and can be read concurrently with magnetically stored data, an additional 15%–20% of the disk is made available to store data (i.e., the portion of the disk previously used for embedded magnetic servo information).

Figure 4:
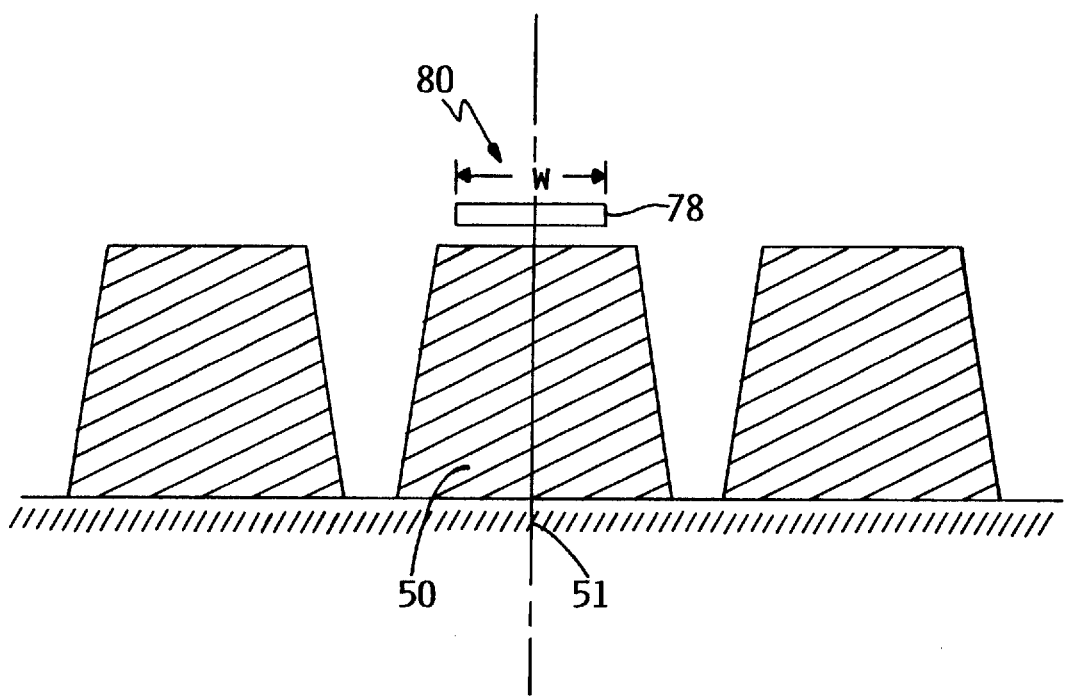
FIG. 4 is a cross-sectional view of a magnetoresistive element of a transducer shown in an on-track orientation over the centerline of a track of a disk.

Turning now to FIG. 4, there is shown an illustration of an MR element 78 of an MR head 80 oriented over the centerline 51 of a track 50. The MR head 80 may be a type used in conventional data storage systems, thus promoting the employment of the present invention in conventional storage systems. As the MR element 78 passes over the track 50 of the rotating disk 24, magnetic transitions developed on the disk 24 surface result in the production of a readback signal induced in the MR head 80. By way of example and not of limitation, the readback signal is preferably a voltage signal.

Figure 5:
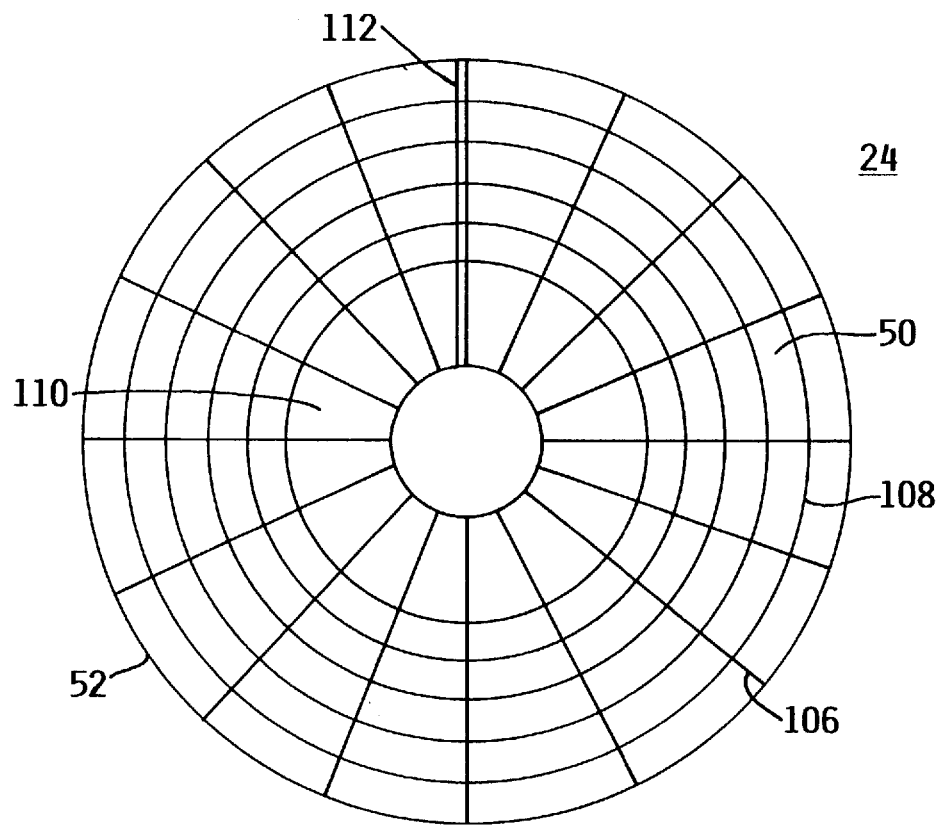
FIG. 5 is a top view of a disk in accordance with the present invention.
Figure 6:
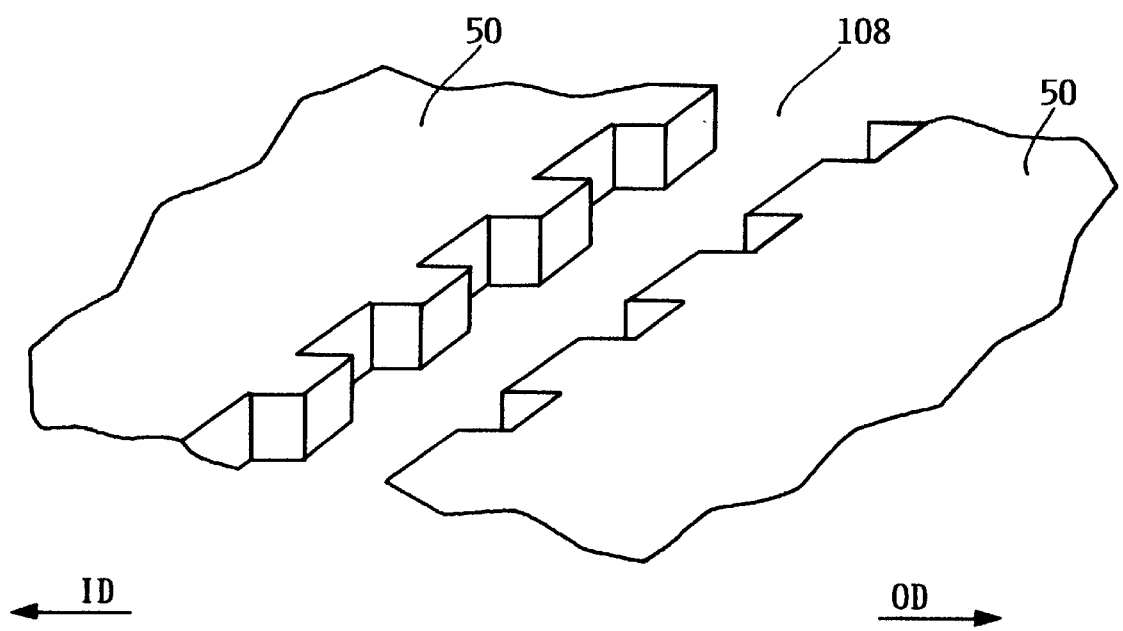
FIG. 6 is a perspective view of two adjacent tracks of a disk separated by a track marker.
Figure 7:
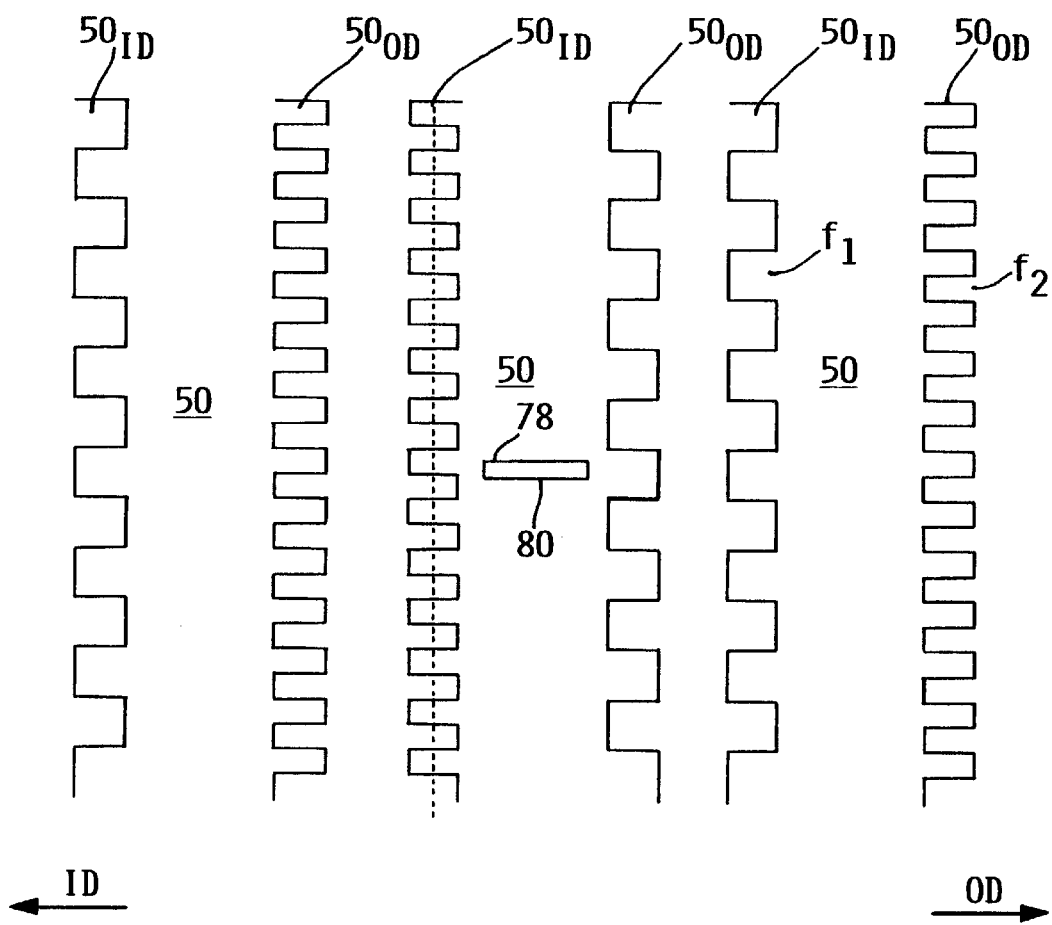
FIG. 7 is a top view of a series of tracks and track markers of a disk.

In FIG. 5, there is illustrated an exemplary disk 24 having pre-embossed or stamped track markers 108 and sector markers 106 for providing servo information on the disk in the form of surface profile variations, e.g. head-to-disk spacing. The disk 24 is provided with concentric data tracks 50 used to store data. Each data track 50 may be partitioned into a series of sectors 52 identified by sector markers 106. Adjacent data tracks 50 are separated by track markers 108. The track markers 108 and the sector markers 106 are formed as variations in the disk 24 which can be identified using the thermal component of the MR head readback signal. As best shown in FIGS. 6 and 7, the track markers 108 may be circumferential grooves providing head-to-disk spacing variations between adjacent data tracks 50 and the sector markers 106 may be radial grooves providing head-to-disk spacing variations between adjacent sectors 52. As described more fully below, the track markers 108 and sector markers 106 are used to provide servo information. The disk 24 is also provided with a calibration zone 110 and an index marker 112, which may be formed by a closely spaced pair of sector markers 106. The purpose of the calibration zone 110 and the index marker 112 will become apparent later.

As shown in FIG. 7, the data tracks 50 of disk 24 are provided with serrated edges $50_{ID}$ and $50_{OD}$ corresponding to the inner diameter (ID) and outer diameter (OD) edges of the track. For each track, the ID edge $50_{ID}$ serration has a different serration frequency than the OD edge $50_{OD}$ serration in order to provide radial direction servo information. The serrations may have the shape of a square wave or a sinusoidal wave. The serrations may have frequencies $f_1$ and $f_2$ which differ by a factor of two, though it should be appreciated that the serrations may have a multitude of different frequencies provided each track has edges $50_{ID}$ and $50_{OD}$ at different frequencies. The serrated edges $50_{ID}$ and $50_{OD}$ of the tracks 50 may alternate in serration frequency, as shown in the illustration. For example, some tracks 50, referred to as odd tracks, may have an (ID) edge $50_{ID}$ at serration frequency $f_1$ and an (OD) edge $50_{OD}$ at serration frequency $f_2$. While even data tracks 50, would have OD edges $50_{OD}$ at frequency f1 and ID edges $50_{ID}$ at frequency f2. By alternating the serration frequencies of adjacent data tracks 50, the serration edges of adjacent tracks 50 correspond. This makes track markers 108, which separate adjacent tracks 50, easier to detect, and the disks 24 easier to manufacture.

Furthermore, the serrations may be aligned radially, i.e. the serrations may be spaced further apart as one moves radially outward. This would be useful in a constant angular velocity system as the serration frequencies relative to the MR head 80 would be constant over the entire surface of the disk 24. In addition, the number of serration cycles around a data track 50 may be a power of two such that data storage system oscillator frequency can be divided to exactly yield each of the serration frequencies $f_1$ and $f_2$.

Figure 8:
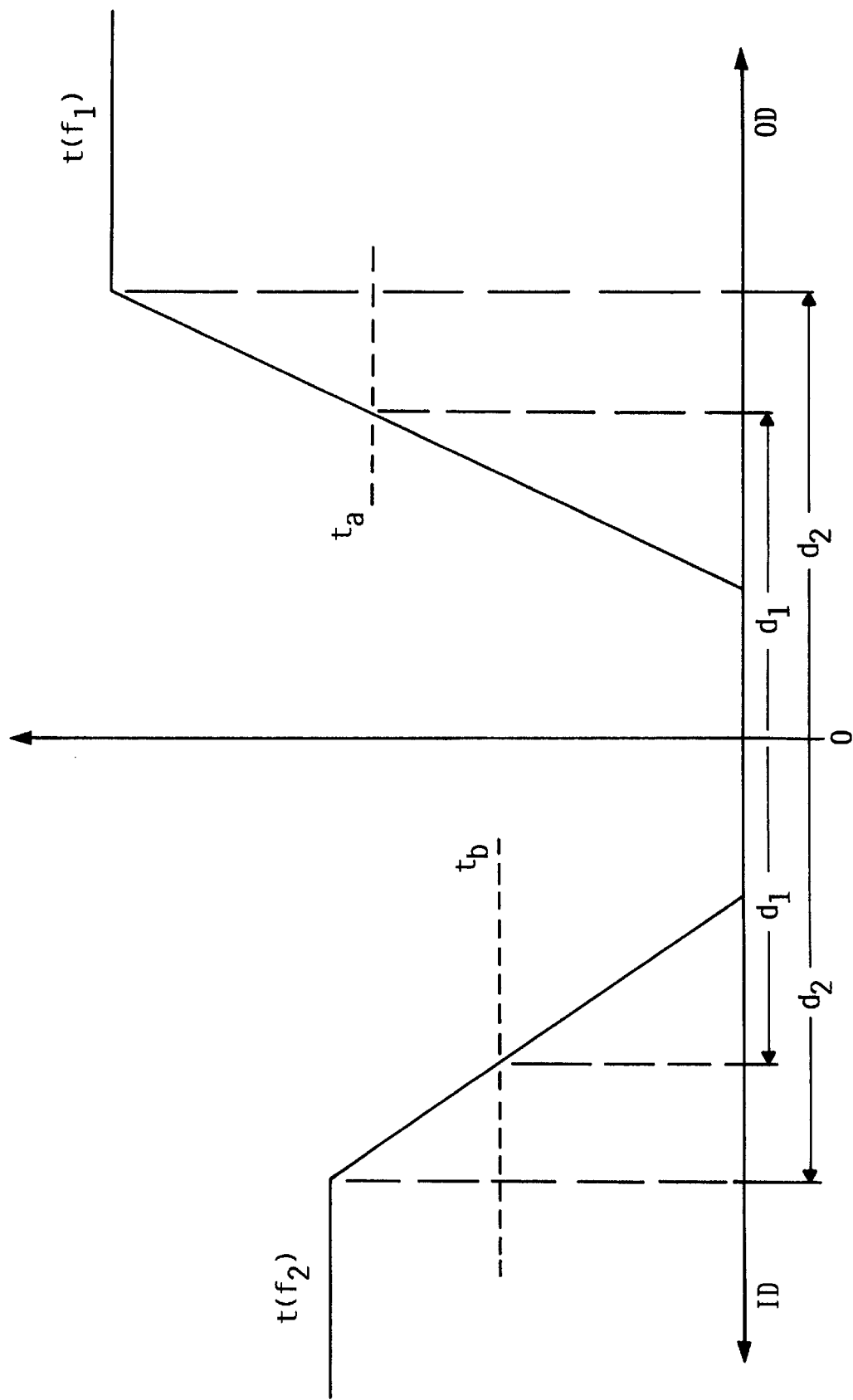
FIG. 8 is an illustration of thermal frequency magnitude responses of an MR head as a function of the MR head position over a track of a disk.

In FIG. 8, the frequency magnitude responses $t(f_1)$ and $t(f_2)$ of the thermal component of the MR head readback signal are illustrated as a function of the position of the MR head 80 over an even data track 50, i.e., a data track 50 having a frequency f2 at ID edge $50_{ID}$ and a frequency $f_1$ at OD edge $50_{OD}$. When the MR head 80 is positioned over the center 51 of the data track 50, the thermal frequency magnitude responses $t(f_1)$ and $t(f_2)$ should be near zero. As the MR head 80 moves off toward the ID edge $50_{ID}$ of an even track 50, the MR head 80 senses the edge serrations and the thermal signal t(f2) increases. Similarly, as the MR head 80 moves toward the OD edge $50_{OD}$, the thermal signal t(f1) increases. It is noted that as the head continues to move off-track, the thermal signals $t(f_1)$ and $t(f_2)$ plateau. As described more fully below, by examining the frequency content of the thermal component of the readback signal, the off-track direction and magnitude of the MR head 80 can be determined and an appropriate control signal provided to position the actuator 30 over the centerline of a track.

It should be appreciated that the thermal frequency magnitude responses $t(f_1)$ and $t(f_2)$, from which the servo information is obtained, are derived from periodic changes in the spacing between the disk 24 and the MR head 80. In the illustrated embodiment, the servo information is obtained from sensing the changes in the thermal frequency response that result from the MR head 80 passing over serrated, circumferential grooves. The change in disk-to-head spacing could alternately be accomplished by providing elevated portions between the tracks. However, in a typical environment, grooves are preferred because they permit operation of the storage system 20 with minimal spacing between MR heads and data tracks. In alternate embodiments of the present invention, servo information is derived from other variations in disk characteristics which can be reflected in the thermal component of the readback signal. For example, the track markers 108 could differ from the data tracks 50 in thermal emissivity or other parameters which can be reflected in the thermal component. Similar variations in disk characteristics can be used for the sector markers 106.

Figure 9:
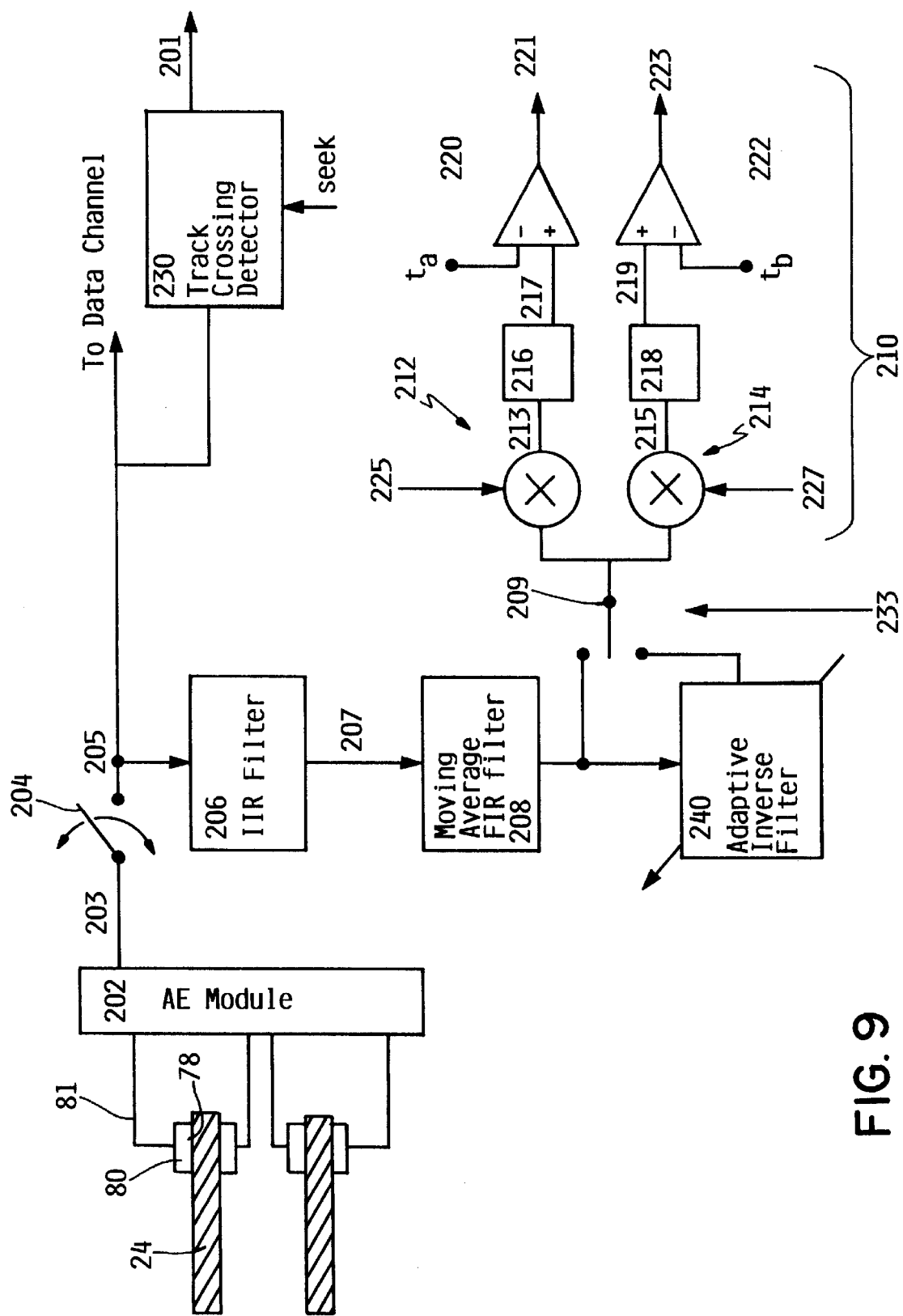
FIG. 9 is a block diagram of a system of components for demodulating the readback signal of an MR head.

Turning to FIG. 9, there is illustrated an exemplary block diagram of a system of components for demodulating a readback signal and generating servo positioning control signals 221 and 223. Although the demodulation system illustrated in FIG. 9 is implemented as a digital system, an equivalent analog system may also be used.

In operation, the demodulation system amplifies the readback signal 81 obtained using the MR head 80. The amplification may be done, for example, by using an Arm Electronics (AE) module 202. The amplified readback signal 203 is sampled by sampler 204 at a sampling rate to produce readback signal 205. A typical sampling rate will be in excess of 100 megahertz (MHz). The sampled readback signal 205 is provided to the data channel for normal processing and also provided to a track crossing detector 230 for purposes to be described hereinafter. The readback signal 205 is also provided to a filter 206, e.g., an inverse infinite impulse response (IIR) filter, to compensate for the highpass filter in the AE module 202. The output signal 207 of the filter 206 is passed through a filter 208, e.g., a moving average low-pass finite impulse response (FIR) filter, to recover the thermal component of the readback signal. The output of filter 208 is provided to a heterodyne demodulation circuit 210, which determines whether thermal frequency magnitude components $t(f_1)$ and $t(f_2)$ of the readback signal 81 exceed their respective threshold values $t_a$ and $t_b$. The operation of the heterodyne demodulation circuit 210 is more fully explained hereinbelow.

During a read operation, the signal 209 received by the heterodyne demodulation circuit 210 is provided directly from filter 208. However, during a write operation, the write element generates heat which is transferred to the MR head. The write head-to-MR head heat transfer distorts the thermal component of the readback signal. The dynamics of the write head-to-MR head heat transfer may be approximated by a first order lowpass filter transfer function. The distortion caused by the write head-to-MR head heat transfer may be substantially reduced by passing the signal leaving filter 208 through an adaptive inverse filter 240 having a transfer function inverse to that of the lowpass filter transfer function. A signal 233 indicative of a read or write operation may be provided to selectively couple the adaptive inverse filter 240. For example, during a write operation, the signal 233 may be used to couple the adaptive inverse filter 240 such that the signal leaving filter 208 is passed through the adaptive inverse filter 240 prior to being received by the heterodyne demodulation circuit 210. During a read operation, the signal 233 may be used to pass the signal leaving filter 208 directly to the heterodyne demodulation circuit 210.

The pole location of the adaptive inverse filter 240 transfer function may vary between MR heads. The pole location for a given MR head may be estimated by using the thermal cooling response of the MR head after a write operation has commenced. For example, the cooling curve may be a simple decaying exponential with a time constant which can be determined from the time it takes the cooling curve to reach approximately 36.8%, i.e., $e^{-1}=0.368$, of its maximum value. The time constant, or pole location value which is the inverse of the time constant, may be estimated in-situ for each MR head and stored in a random access memory (RAM). The adaptive inverse filter 240 transfer function may then be updated based on the time constant of the MR head which is selected. The transfer function of the adaptive inverse filter 240 for each MR head may be updated over time to account for changes in the write head-to-MR head and MR head-to-disk heat transfer dynamics which may result from debris collecting on the heads.

The adaptive inverse filter 240 thus restores the distorted thermal component to that which would be present during a read operation. Using a readback signal having its thermal component restored by an adaptive inverse filter 240 as an input to the heterodyne demodulation circuit 210, decreases track misregistration (TMR) during writing. Moreover, the continuous nature of the servo position sensing, i.e., sensing during both read and write operations, eliminates the need to use accelerometers or other external sensors to monitor shock and vibration in a drive.

The heterodyne demodulation circuit 210 comprises first and second multipliers 212 and 214, filters 216 and 218, and first and second comparators 220 and 222. The heterodyne demodulation circuit 210 extracts the thermal frequency magnitude response signals $t(f_1)$ and $t(f_2)$ from signal 209 and compares these signals to threshold values $t_a$ and $t_b$ to generate servo positioning control signals 221 and 223.

In operation, the heterodyne demodulation circuit 210 receives signal 209 and provides it to first and second multipliers 212 and 214. Multipliers 212 and 214 multiply the readback signal 209, with two or more divided oscillator signals 225 and 227, respectively. The oscillator signals 225 and 227 may have waveforms and frequencies similar to the serration frequencies of the serrated edges generated when the disks 24 are rotated at rated speed. The multipliers 212, 214 output signals 213 and 215 which have amplified frequency components at frequencies $f_1$ and $f_2$, respectively. Signals 213 and 215 are low-pass filtered by filters 216 and 218, thereby rejecting the high frequency components of signals 213 and 215 to generate low frequency thermal magnitude response signals $t(f_1)$ and $t(f_2)$, designated 217 and 219, respectively. Thermal signals 217 and 219 are provided to comparators 220 and 222, for comparison with threshold values $t_a$ and $t_b$.

As best shown in FIG. 8, threshold values $t_a$ and $t_b$ correspond to the threshold amplitudes of thermal signals $t(f_1)$ and $t(f_2)$ at which an MR head 80 has moved off-track and should be repositioned. It is noted that threshold values $t_a$ and $t_b$ are predetermined values for each MR head 80 and are stored in a random access memory (RAM). The threshold values $t_a$ and $t_b$ are determined in consideration of differences in thermal sensitivity along the width W of an MR element for different MR heads 80 and may be different for different MR heads, as discussed more fully hereinafter.

Comparator output signals 221 and 223 from comparators 220 and 222 may have a logical value of 0 or 1. When the MR head 80 is centered over a track 50, both outputs 221, 223 may assume a logical value of 0, for example. If the thermal frequency response signal 217 exceeds threshold value $t_a$, then comparator output signal 221 may assume a logical 1. Similarly, if signal 219 exceeds threshold $t_b$, then comparator output signal 223 may have a logic of 1. If signals 217 and 219 have frequency components at serration frequencies $f_1$ or $f_2$ below their respective thresholds, then both comparator outputs 221 and 223 will be zero. As described hereinafter, comparator outputs 221 and 223 may be used by a track follow servo control system to control the position of the MR head 80.

Figure 10:
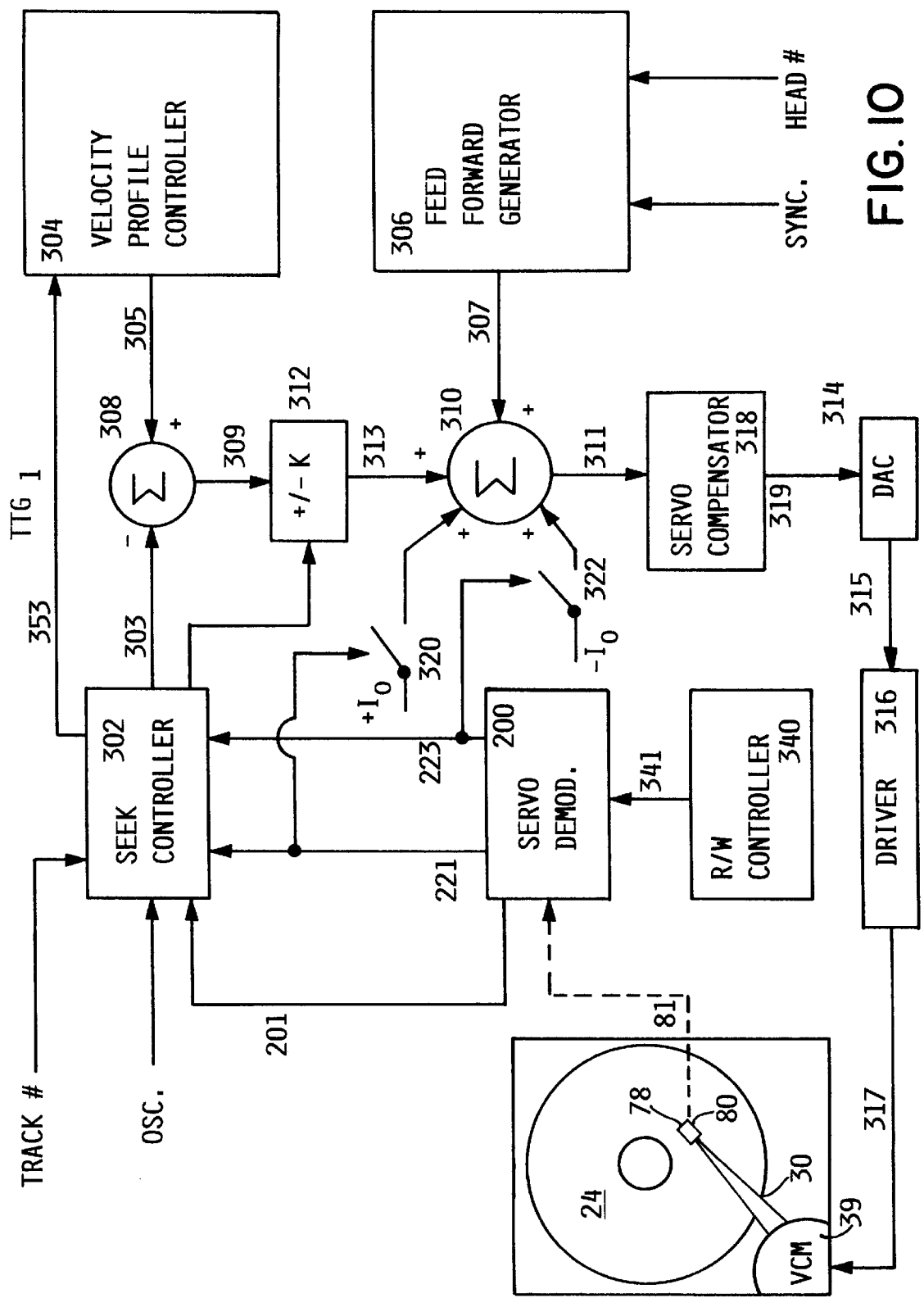
FIG. 10 is a generalized block diagram of the system components for servo positioning an MR head using the thermal frequency response signals of the MR head in accordance with the present invention.

Referring now to FIG. 10, there is illustrated an exemplary servo control system using comparator signals 221 and 223 for servo positioning the MR head 80 over a data track 50. The servo control system includes a servo demodulator 200, a read/write (R/W) controller 340, a seek controller 302, a velocity profile controller 304, a feed-forward generator (FFG) 306, first and second adders 308 and 310, a multiplier 312, a servo compensator 318, a digital to analog converter (DAC) 314, and a driver 316.

In operation, the R/W controller 340 provides signal 340 to the servo control system, e.g. to the servo demodulator 200. Signal 340 may be used to control the type of operation or mode, e.g. read/write, or track follow, seek, or settle. During track following, for example, the comparator output signals 221 and 223 control switches 320 and 322, respectively, for coupling digital values $+I_o$ and $-I_o$ to the adder 310. When comparator output 221 assumes a logical 1, switch 310 is configured to close so that the value $+I_o$ is provided to the adder 310. Similarly, the value $-I_o$ is provided to the adder 310, when the comparator output signal 223 assumes a logical 1. The digital values $+I_o$ and $-I_o$ are provided as pulsed injection values to control movement of the actuator. If both comparator output signals 221 and 223 are zero (0), both switches 320 and 322 remain open and no pulsed injection is provided to the adder 310. It is noted that, if both comparator outputs assume a logical 1, there is an error and the comparator outputs can be ignored.

The adder 310 sums the pulsed injection value $+I_o$ or $-I_o$, if any, with a feed-forward generator (FFG) value 307 and provides the summed signal 311 to the servo compensator 318. It is noted that though the adder 310 is configured to receive signal 313, this signal may be ignored or not provided in track following operations as it is primarily used in track seeking, as described below. The FFG value 307 represents MR head axial offset and track runout as a function of disk 24 rotation and is provided to the adder 310 by the feed-forward generator (FFG) 306. The FFG 306 stores the predetermined MR head 80 axial offset and track runout for each MR head 80 of a storage device in a Random Access Memory (RAM). The track runout and head offset for each MR head 80 may be determined using a calibration procedure set forth below.

The servo compensator 318, typically a micro processor, processes signal 311, and, taking into account the type of data track 50, i.e. odd or even, generates a servo positioning control signal 319. The control signal 319 is converted to an analog signal 315 by the DAC 314 and provided to the driver 316, which in response provides a current 317 to the voice coil motor (VCM) 39 to move the actuator 30. In this manner, movement of the actuator 30 is controlled so that the MR head 80 follows a given data track 50.

The servo control system may also be used for track seeking, i.e. moving a MR head 80 to a location over a specified track 50 of a disk 24. In a track seeking operation, the servo control system uses the velocity difference between an estimated radial velocity of the MR head 80 and a desired radial velocity to generate a signal for controlling the radial velocity of the actuator arm 30 and thus the MR head 80. For example, if the estimated velocity is less than the desired velocity, the servo compensator 318 generates a signal to increase the radial velocity of the MR head 80 by increasing the rotation of the actuator arm 30. Conversely, if the desired MR head 80 velocity is less than the estimated MR head 80 radial velocity, the servo compensator 318 generates a signal to decrease the radial velocity of the actuator arm 30.

The seek controller 302 generates an estimated head velocity (EV) signal 303 which is subtracted by adder 308 from a desired head velocity (DV) signal 305 generated by the velocity profile controller 304. The velocity difference (DV−EV) signal 309 is multiplied by a velocity gain +K or −K in multiplier 312 and the product 313 is provided to the adder 310. The seek controller 302 may also provide a seek direction signal 300 for use by multiplier 312 to determine whether velocity gain −K or +K is used. The adder 310 adds the velocity difference signal 313 to the feed-forward generator (FFG) value 307 and provides the sum value 311 to the servo compensator 318, which processes the value 311 and generates a servo positioning control signal 319. Control signal 319 is converted to an analog signal 315 by the DAC 314 and provided to the driver 316. The driver 316 generates a current 317 for the VCM 39 of the actuator assembly 37, thereby increasing or decreasing the radial velocity of the MR head 80 so that the MR head 80 can efficiently seek and be positioned over the desired location.

The seek controller 302 generates the estimated head velocity by measuring the time between readback signal 81 magnetic component dropouts, which occur as the MR head 80 passes over the track markers 106, and dividing this time into the fixed track pitch using oscillator pulses. This velocity estimate may be further refined by compensating for the track runout of the MR head 80. Such further refinement may be done at low head velocities, for example, when the MR head 80 is settling onto a specified data track 50. It is noted that the estimated velocity may also be determined using thermal component peaks which, similar to magnetic dropouts if the disk 24 is magnetically recorded, occur over track markers 106. The magnetic components, however, provide a higher signal-to-noise ratio.

In addition to estimating MR head 80 velocity, the seek controller 302 keeps account of the track number of the current data track over which the MR head 80 is positioned and also counts data track crossings. Data track crossings are counted in a track crossing detector 230, as shown in FIG. 9, by amplitude detecting the thermal component peaks or the magnetic component dropouts in the readback signal which occur as the track markers 106 are traversed by the recording head. Each time the head crosses a track marker 106 a pulse is generated on line 201 at the output of track crossing detector 230. The seek controller 302 uses current track number and track counting to determine the difference between the current data track number over which the MR head 80 is positioned and the targeted data track number which the MR head 80 is seeking. This track number difference is referred to as the number of tracks-to-go (TTG) and is provided by the seek controller 302 to the velocity profile controller 304. During a seek operation the seek controller 302 counts track crossing pulses present on line 201, and continues to update the TTG count signal 353. As the TTG signal approaches zero, i.e., as the MR head nears the target track, the radial velocity decreases rapidly and the actuator control may switch into a settle mode where the track following demodulator outputs 221 and 223 may be used jointly with the track crossing detector outputs for velocity estimations. The switch to settle mode may be triggered if TTG is below a certain count, e.g., TTG <1–2 tracks.

The velocity profile controller 304 receives a TTG signal 353 and uses it to determine the desired velocity of the MR head 80. The desired head velocity is determined from a relationship between the desired head velocity and TTG. This relationship is predetermined and may be stored in a look-up table in RAM coupled to the velocity profile controller 304.

The servo control system advantageously provides continuous servo control as the thermal component of an MR head 80 can be sampled concurrently with the magnetic signal component. Unlike traditional magnetic servo techniques, thermal servoing can reach sampling rates in excess of 100 KHz. The higher sampling rates of thermal servoing provide for smaller actuator coil currents. Moreover, due to the mechanical inertia of the actuator, these small currents are integrated to produce very smooth motions, thereby reducing actuator jerk. The finer actuator control allows for higher track densities (approaching 16,000 tracks per inch for a dual actuator) and significantly improves the detection of shock and vibration in a disk 24. In addition, for predictive failure analysis (PFA) purposes, any defect on a disk 24 which might potentially create track misregistration (TMR) can be detected. Similarly, any random MR head 80 modulation, e.g., modulation caused by an MR head 80 that is not lifting off the disk 24, can be detected.

It is noted that using pre-embossed disks 24 requires that the servo information be formed on the disk prior to assembly into the disk drive. When multiple disks are used, the alignment of servo information from disk to disk must be taken into account. For example, due to mechanical tolerances in the manufacture of the disks 24 and the mounting of the disks 24 in a storage device, each disk 24 in the disk pack likely has a different eccentricity or runout. In addition, mechanical tolerances will cause axial offsets between the MR heads 80. Thus, a calibration procedure is needed to determine individual disk runout, MR head axial offsets, and rotational position alignment differences with respect to the radial index markers 112.

To calibrate and format disks 24 in a storage device, each disk 24 is provided with an annular calibration zone 110 which can be located anywhere on the disk 24, for example, at the outer diameter (OD) crash stop of the disk 24 or at the inner diameter (ID) crash stop of the disk 24. The calibration zone 110 must have a width at least as large as the worst case eccentricity of the disk 24 plus the maximum MR head axial offset. An exemplary width is 32 tracks.

Figure 11B:
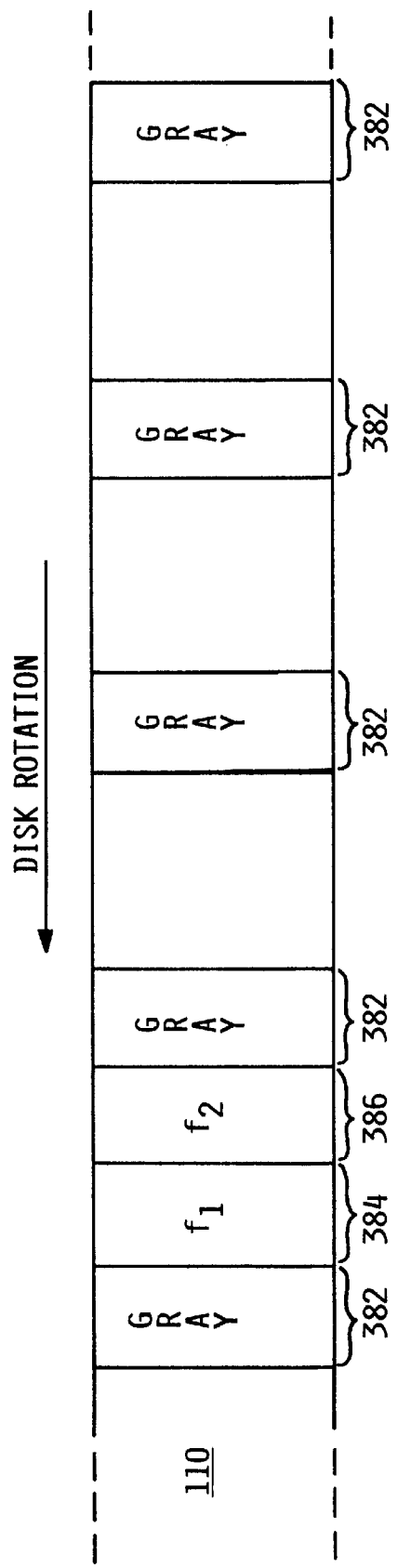
FIG. 11(b) is a detailed view of a segment of a calibration zone.

As illustrated in FIGS. 11(a) and 11(b), the calibration zone 110 consists of a repeating Gray code pattern, which may be equally spaced and have six to eight bits. The Gray code pattern may be interlaced by blank space or by frequency patterns 384 and 386. The gray code pattern 382 and the frequency patterns 384 and 386 consist of variations in disk characteristics, which may be thermally readable. In the illustrated embodiment, the gray code pattern 382 is encoded as embossed depressions and the frequency patterns 384 and 386 comprise radial grooves. The MR head 80 will thermally respond to a depression or groove with a positive spike-like signal.

It is noted that patterns illustrated in FIGS. 11(a) and 11(b) have a linear density on the disk such that their frequency at a rated disk velocity is commensurate with the frequency range of the thermal signal. For example, while magnetic frequencies are typically on the order of 100–200 MHz, the thermal frequencies are significantly less, e.g., the patterns may have a frequency of 100–200 kHz.

A segment of an exemplary calibration zone 110 is illustrated in FIG. 11(a). The segment shows eight tracks labelled n−2, n−1, n, n+1, n+2, . . . , n+5, a four bit Gray code labeled $\{b_3, b_2, b_1, b_0\}$, and frequency patterns 384, 386. The Gray code, which may be written on ½ track width pitches with ¼ track width offset, are designated by . . . j−2, j−1, j+1, . . . In the exemplary illustration of FIG. 11(a), the MR head 80 is located on calibration zone track n+2. As the head traverses the Gray code ½ track (j+4), two positive spikes $\{b_3, b_2\}$ result. Since a smaller portion of the head traverses Gray code ½ track (j+3), a smaller spike ($b_0$) results. The spikes are compared to a threshold, and if the threshold is exceeded, a logical 1 may be output, otherwise a logical 0 may be output. For example, in the illustrated embodiment, if only spikes ($b_3$, $b_2$) exceed the threshold, a code $\{1, 1, 0, 0\}$ will be decoded.

The Gray code 382 is processed to determine axial and relative head offset and track runout for each MR head 80 in a storage device. As noted above, head offset and track runouts may be stored in RAM coupled to the feed-forward generator 302 and used in the servo control system for track following and track seeking. The axial offset of an MR head 80 is determined by rotating the disk 24 through one complete revolution and reading the Gray code pattern 382 with the MR head 80, followed by signal averaging. A thermal Gray code signal is created in the readback signal of the MR head 80 as it passes over the Gray code pattern 382 depressions and elevations. The thermal Gray code signal is processed to determine absolute average measurements of disk eccentricity or runout. The axial head offset is determined by averaging the absolute averaged measurements of disk eccentricity of a complete revolution. By doing this, the position of each MR head 80 relative to other MR heads 80 can be determined.

Figure 12:
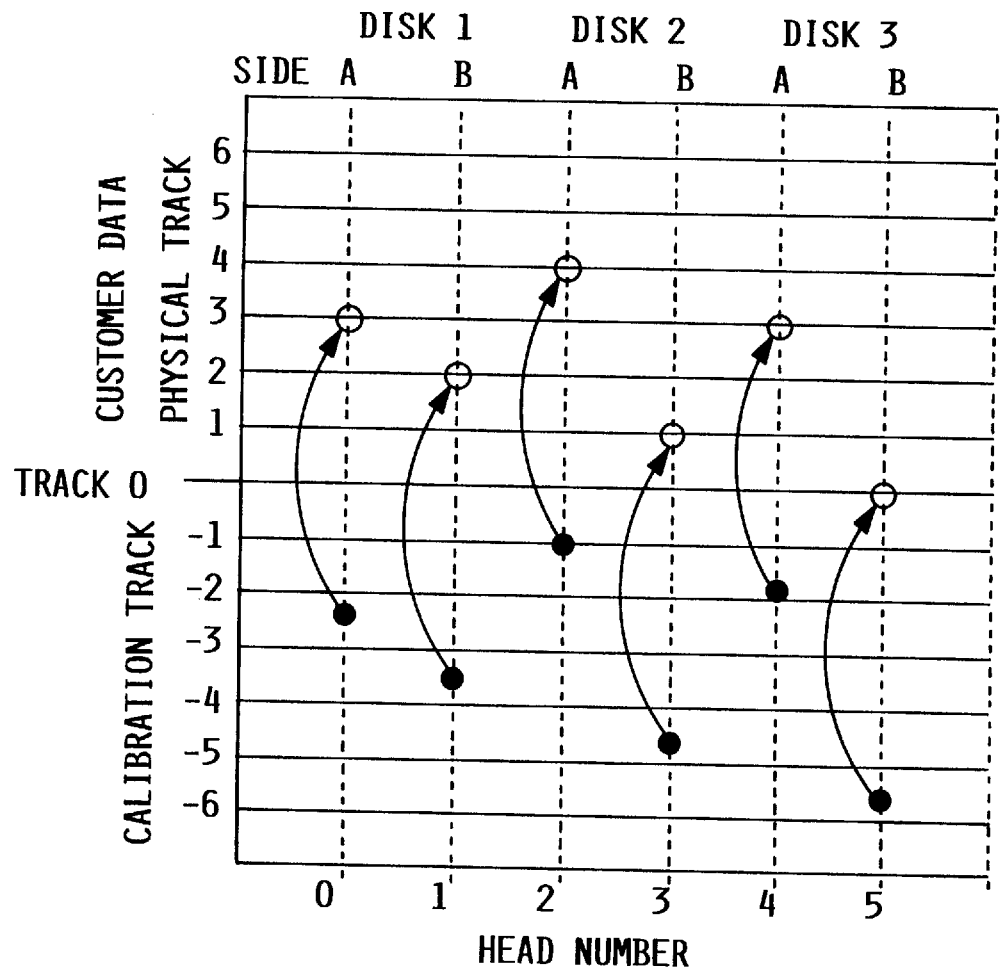
FIG. 12 is a diagram showing the mapping of MR heads to physical tracks for a cylinder.

The axial head offsets may be used in multiple disk systems to determine the physical track of each MR head 80 in a cylinder. It is noted that a cylinder represents the physical tracks over which the MR heads 80 are positioned. In an exemplary arrangement, the physical track zero of the MR head 80 with the largest axial offset is mapped to cylinder zero. MR heads 80 with less axial offset are mapped to higher physical track numbers based on the largest axial offset. An example of this mapping for a storage system having three disks and six MR heads 80 is shown in FIG. 12. The solid circles represent the position of each MR head 80 in the calibration zone 110. The distance between the solid circles and the horizontal axis represents the axial offset of each MR head 80 from its physical track zero Since MR head number 5 has the largest axial offset of 5.5 tracks, it is mapped to its physical track zero. The remaining MR heads 80 are mapped to physical tracks which are 5.5 tracks spaced from their positions in the calibration zone 110. By mapping cylinder zero to the physical track zero of the MR head 80 with the largest axial offset, the seeking required during head switching is minimized.

The frequency calibration patterns 384 and 386 are used for measuring the thermal sensitivity of the MR heads 80 in order to determine appropriate servo thresholds $t_a$ and $t_b$ for a given head. Servo thresholds $t_a$ and $t_b$ compensate for different thermal sensitivities between MR heads 80 resulting from differences in MR element dimensions, recession, shield spacing and dimensions, MR lead thermal conduction, etc.

To determine the servo thresholds $t_a$ and $t_b$ for each MR head 80 in a storage system, the frequency patterns 384 and 386 have serration frequencies, which, for example, may be equal to the serration frequencies f1 and f2 of serrated edges $50_{ID}$ and $50_{OD}$. The threshold calibration procedure for a multiple disk device includes the following steps. First, all MR heads 80 of a storage system are moved to the calibration zone 110 of their respective disk 24. An MR head 80 is selected and its respective disk 24 is rotated. Thermal frequency magnitude responses $t(f_1)$ and $t(f_2)$ are created as the MR head 80 passes over frequency patterns 384 and 386. Thresholds $t_a$ and $t_b$ may be calculated using thermal frequency magnitude responses $t(f_1)$ and $t(f_2)$. For example, as shown in FIG. 8, the ratio of the thresholds to the plateau amplitudes may be a constant based upon the assumption that thermal sensitivity along the width W of an MR element is constant, or the thresholds may be determined from the relationships: $t_a=k_a t(f_1)$ and $t(f_2)$ and $t_b=k_b t(f_2)$. Thresholds $t_a$ and $t_b$ for the selected MR head 80 are stored in RAM, and the process is repeated for another MR head 80 until threshold values for all MR heads 80 in the storage system have been calculated.

An exemplary calibration procedure for determining the position of all of the index markers 112 on the disk 24 surfaces in a disk pack involves the following steps. An index marker 112 of a reference disk 24 is identified, and the time difference (including head switch time) between the reference disk 24 index marker 112 and an index marker 112 of a second disk 24 is measured. This is repeated until the time difference between all index markers 112, and therefor sectors 52, is established. Advantageously, the relative timing calibration can be performed simultaneously with the thermal signal calibration.

Figure 13:
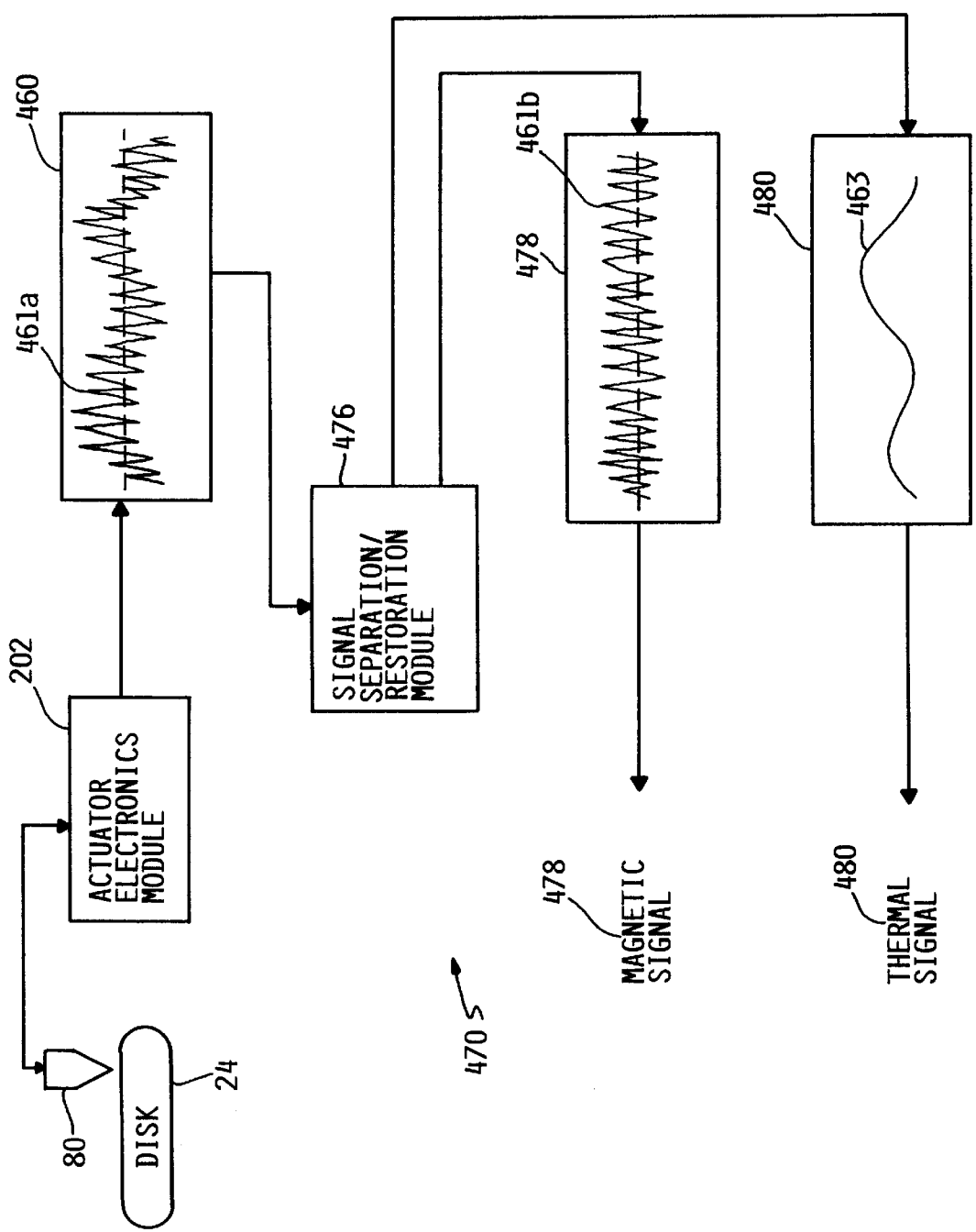
FIG. 13 is a block diagram of an apparatus for extracting a thermal signal from a readback signal induced in an MR head.

Referring now to FIG. 13 there is illustrated an apparatus for reading an information signal having a magnetic signal component and a thermal signal component from a magnetic storage medium and separating the thermal and magnetic signal components from the information signal. An MR head 80 is shown in close proximity with a surface of a data storage disk 24. The readback signal induced in the MR head 80 is typically amplified by the AE module 202. Filtering of the readback signal by the AE module 202 may also be performed. As shown in graphical form at the output of the AE module 202, the analog readback signal 460, containing a relatively high frequency magnetic signal component 461a, exhibits a distorted D.C. baseline due to the presence of a low frequency modulating signal component. It is appreciated by those skilled in the art that a modulated readback signal 460, or more particularly, a modulated magnetic signal component 61a of the readback signal 460 has long been identified as a source of a number of data storage system maladies, including servo control errors and inaccuracies, a reduction in data storing and retrieving reliability, and, in some cases, an irretrievable loss of data.

It has been discovered by the inventors that the readback signal 460 is a composite signal comprising independent magnetic and thermal signal components, and that the low frequency modulating readback signal baseline is in actuality an independent thermal signal component of the readback signal 460. It has further been determined by the inventors, as will also be discussed in detail hereinbelow, that the undesirable readback signal 460 modulation can be eliminated or substantially reduced in magnitude, thus providing for a pure magnetic signal representative of data or servo information.

Figure 14:
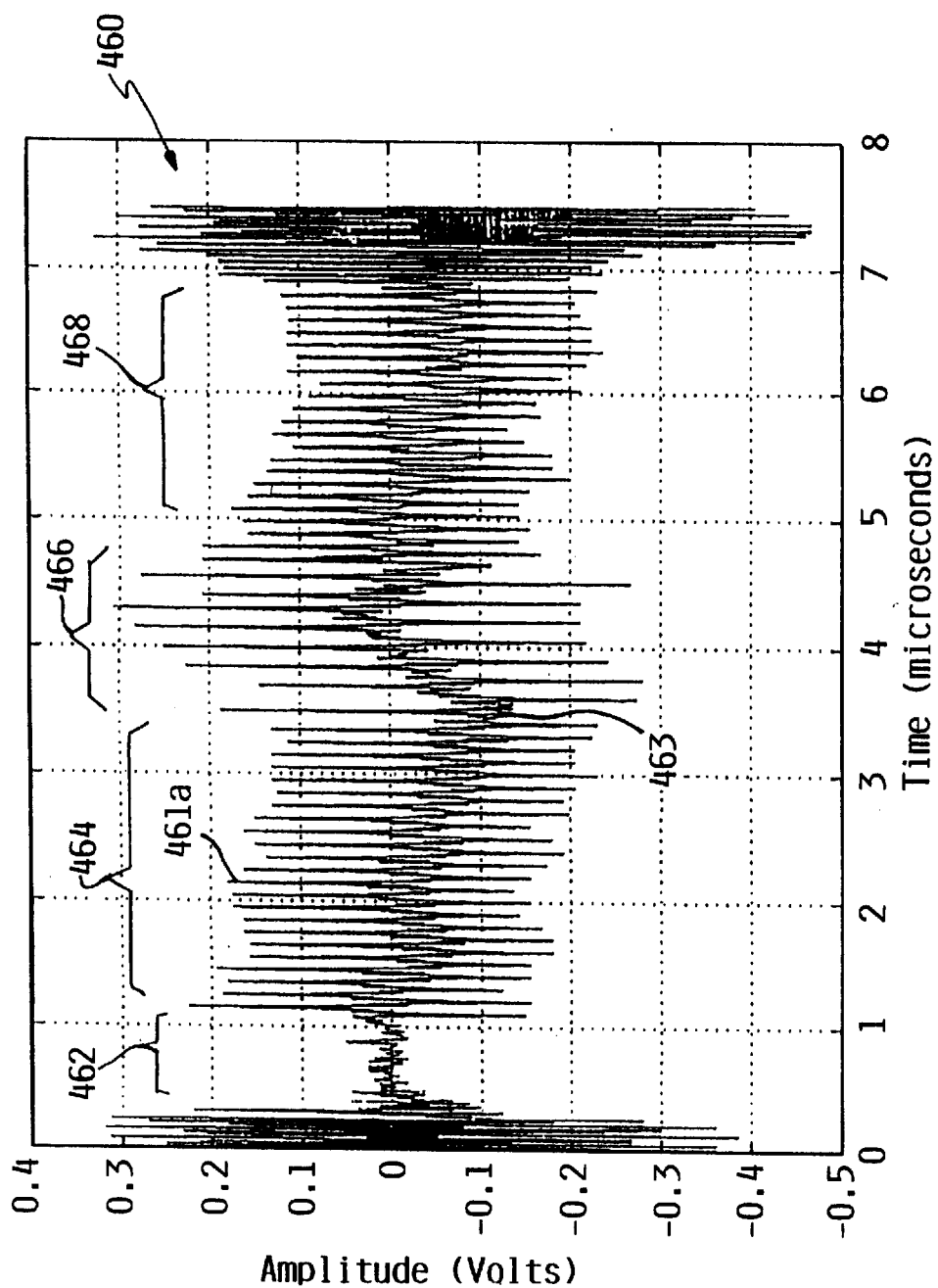
FIG. 14 is a showing of a readback signal induced in an MR head exhibiting a distorted D.C. baseline.
Figure 15:
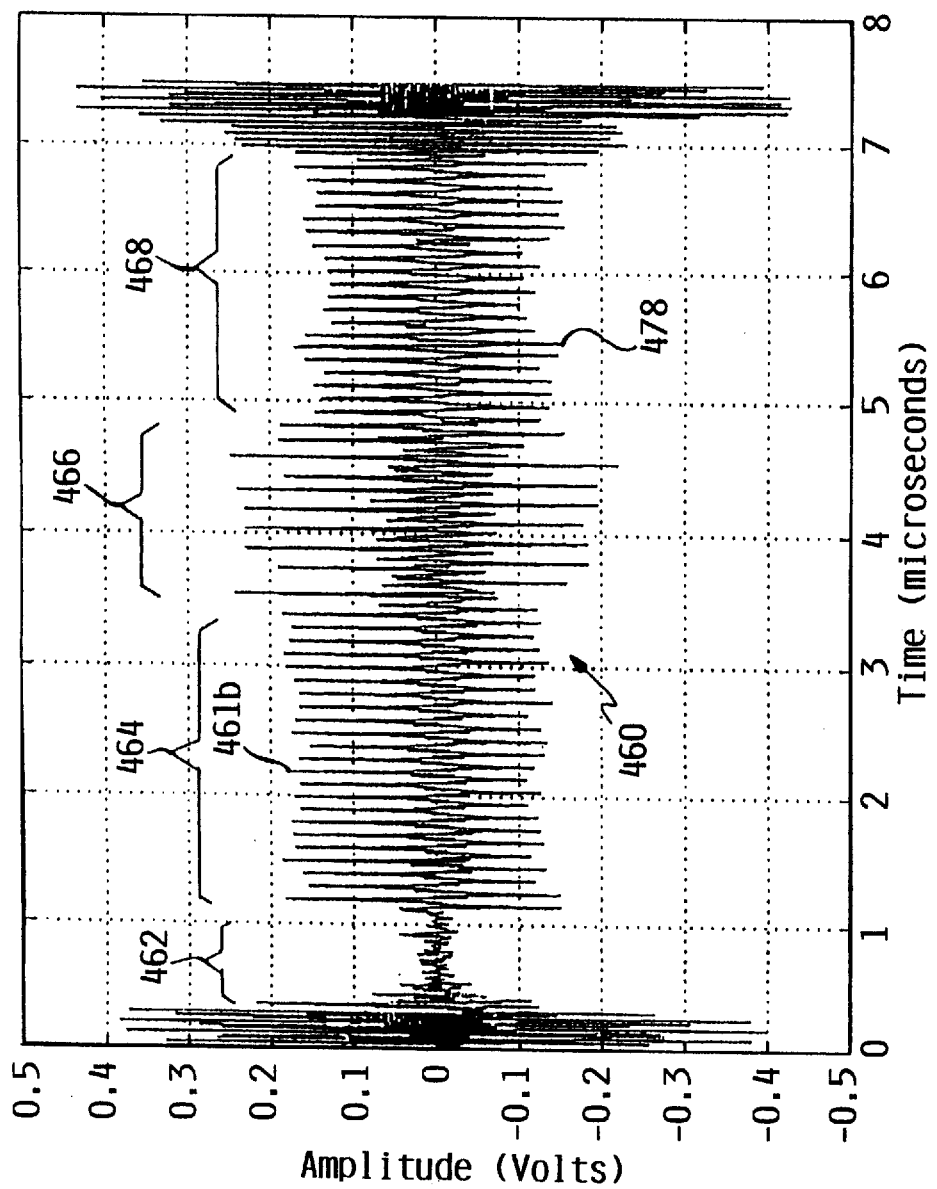
FIG. 15 is a showing of the readback signal of FIG. 14 exhibiting a restored D.C. baseline after being processed by a signal separation/modulation module.

In FIGS. 14 and 15, there is respectively illustrated a distorted readback signal and an undistorted readback signal restored by a signal separation/restoration module 476 as shown in FIG. 13. The signal separation/restoration module 476 processes the readback signal 460 to restore the readback signal baseline, as shown in FIG. 15, by eliminating the undesirable baseline modulation, thereby producing a pure, unperturbed magnetic signal 461b. It is noted that the signal separation/restoration module 476 generally represents the readback signal filter apparatus of the servo demodulator 200 illustrated in FIG. 9 needed to extract the thermal signal from the readback signal.

The independence of the magnetic signal and the thermal signal is demonstrated by the waveforms shown in FIG. 17. The waveform shown in FIG. 17(a) represents the thermal signal extracted from a composite readback signal using an MR head and a digital filter configured as a low pass filter. After the waveform shown in FIG. 17(a) was obtained, the track from which the waveform was generated was subject to AC erasure. The same MR head was moved to the same track location of the erased track to obtain the waveform shown in FIG. 17(b). It can be seen that the extracted thermal signal shown in FIG. 17(a) and the readback signal derived from the erased track shown in FIG. 17(b) are substantially identical. The two waveforms provided in FIG. 17 verify that the two simultaneously read thermal and magnetic signals are independent and separable.

Figure 16:
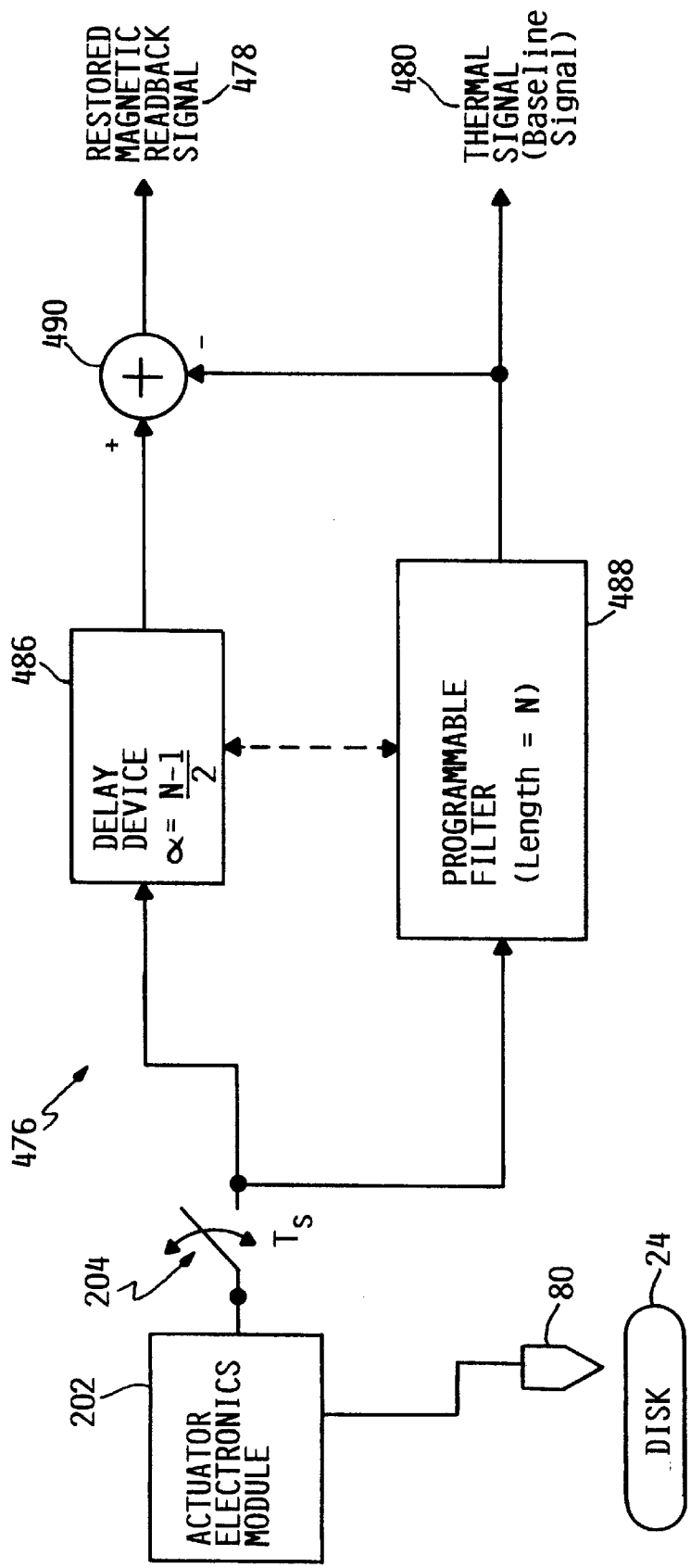
FIG. 16 is a block diagram of a signal separation/modulation module for extracting a thermal signal and a magnetic signal from a readback signal induced in an MR head.

Referring to FIG. 16, there is illustrated an embodiment of a signal separation/restoration module 476 discussed previously with respect to FIG. 13. It is to be understood that the signal separation/restoration module 476 may be employed to perform the single task of separating the independent magnetic signal from the readback signal 460 in order to remove the low frequency modulation component of the readback signal 460 attributed to thermal signal influences. In another embodiment, the signal separation/restoration module 476 may be employed to perform the dual tasks of separating the magnetic signal component from the readback signal 460 to remove low frequency thermal signal component, and, in addition, extracting the thermal signal, thus making available for subsequent processing both the pure magnetic signal and pure thermal signal in independent form.

As shown in FIG. 16, a readback signal is sensed by the MR head 80 situated in close proximity with a magnetic data storage disk 24. In one embodiment, a readback signal received from the AE module 202 from the MR head 80 is converted from analog form to digital form by an analog-to-digital converter 204. The digitized readback signal is then communicated to a delay device 486 and to a programmable filter 488. The programmable filter 488 is a finite impulse response (FIR) filter having a length N, where N represents the number of impulse response coefficients or taps of the programmable filter 488. The readback signal applied to the input of the programmable filter 488 is subject to a total signal delay corresponding to the length N of the programmable filter 488 as the readback signal passes through the programmable filter 488.

In accordance with this embodiment, the programmable filter 488 is programmed with appropriate tap coefficients and weights so as to pass the relatively low frequency thermal signal component of the readback signal and to filter out the relatively high frequency magnetic signal component. As such, the programmable filter 488 is configured as a low pass filter and programmed to pass the thermal signal which can be generally characterized as a medium frequency signal with much of its energy in the frequency range of approximately 10 kilohertz (KHz) to approximately 100–200 KHz. It is noted that the magnetic signal component of the readback signal has a frequency ranging between approximately 20 megahertz (MHz) and 100 MHz. The thermal signal 480 at the output of the programmable filter 488 is communicated to a signal summing device 490. From the output of the programmable filter 88, the thermal signal 480 may be transmitted to other components in the data storage system, such as a servo control for purposes of controlling track following and track seeking operations.

The delay device 86 receives the readback signal 460 from the analog-to-digital converter 204 and delays the transmission of the readback signal to the signal summing device 490 by a duration of time equivalent to the delay time required for the readback signal 460 to pass through the programmable filter 488. As such, the readback signal 460, containing both magnetic and thermal signal components, and the thermal signal 480, extracted from the readback signal by the programmable filter 488, arrive at the signal summing device 490 at substantially the same time. The signal summing device 490 performs a demodulation operation on the readback signal 460 and thermal signal 480 to produce a restored readback signal 478. Thus, the signal separation/restoration module 476 illustrated in the embodiment depicted in FIG. 16 provides for the separation of the magnetic and thermal signal components of a composite readback signal and, additionally, produces a non-distorted restored magnetic readback signal 478. For more details on designing, implementing, and programming a FIR filter for use in the signal separation/restoration module 476, reference is made to E. C. Ifeachor, B. W. Jervis, "Digital Signal Processing" (Addison-Wesley Publishing Company, Inc. 1993).

Returning to FIGS. 14 and 15, the modulated readback signal 460 shown in FIG. 14 represents the appearance of the readback signal prior to being processed by the signal separation/restoration module 476. The representation of the readback signal in FIG. 15 is a showing of the readback signal of FIG. 14 after being processed by the signal separation/restoration module 476. The undesirable influence of the thermal signal component of the distorted readback signal shown in FIG. 14 was eliminated by employing a 9-tap FIR filter in the signal separation/restoration module 476 in order to produce the restored magnetic readback signal 478 shown in FIG. 15. The magnitude and phase characteristics of the 9-tap FIR filter utilized to produce the restored magnetic readback signal 478 shown in FIG. 15 are illustrated in FIG. 19.

Figure 18A:
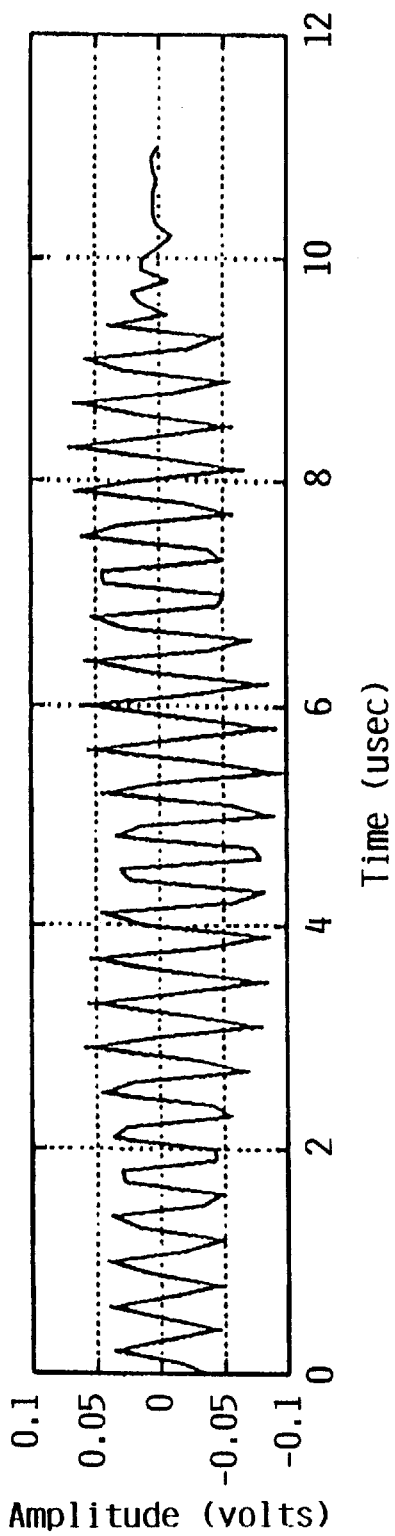
FIGS. 18(a), 18(b) and 18(c) respectively illustrate a readback signal induced in an MR head, a restored magnetic signal component of the readback signal, and an unrestored magnetic signal component of the readback signal.
Figure 18B:
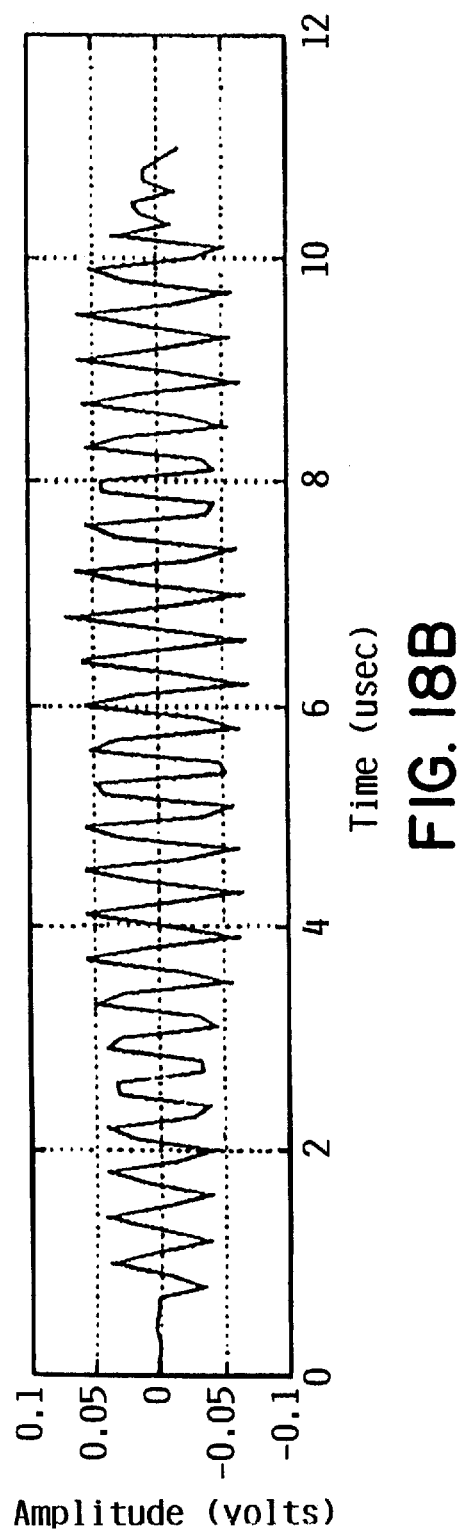
Figure 18C:
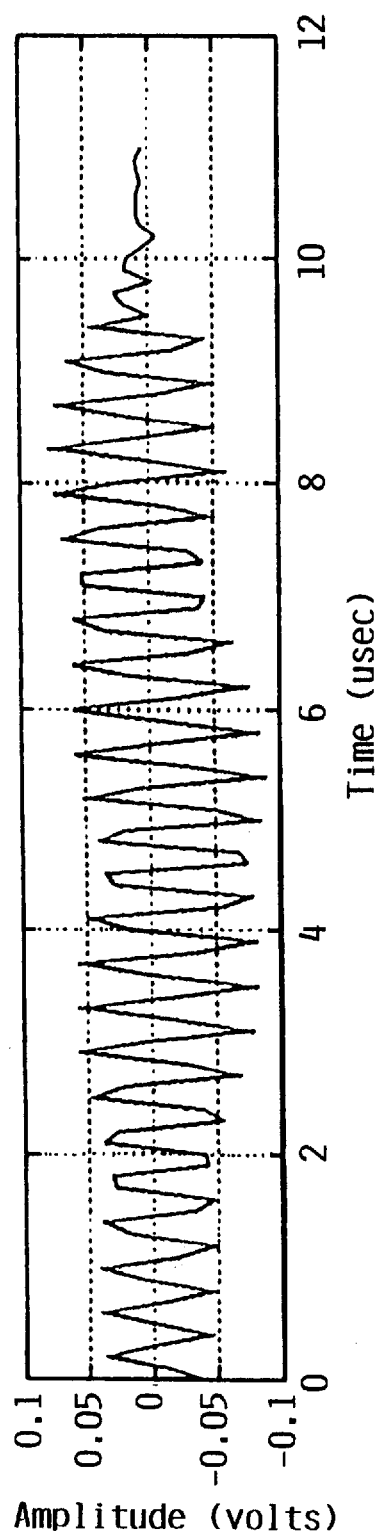
Figure 19A:
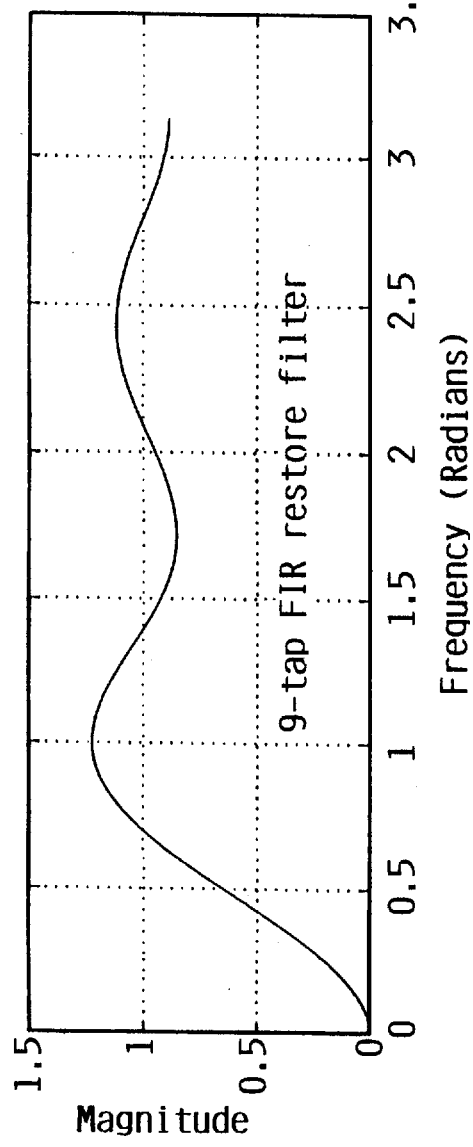
FIGS. 19(a) and (b) and 20(a) and 20(b) illustrate the phase and magnitude response of a finite impulse response (FIR) filter and a windowed FIR filter used in a signal separation/restoration module.
Figure 19B:
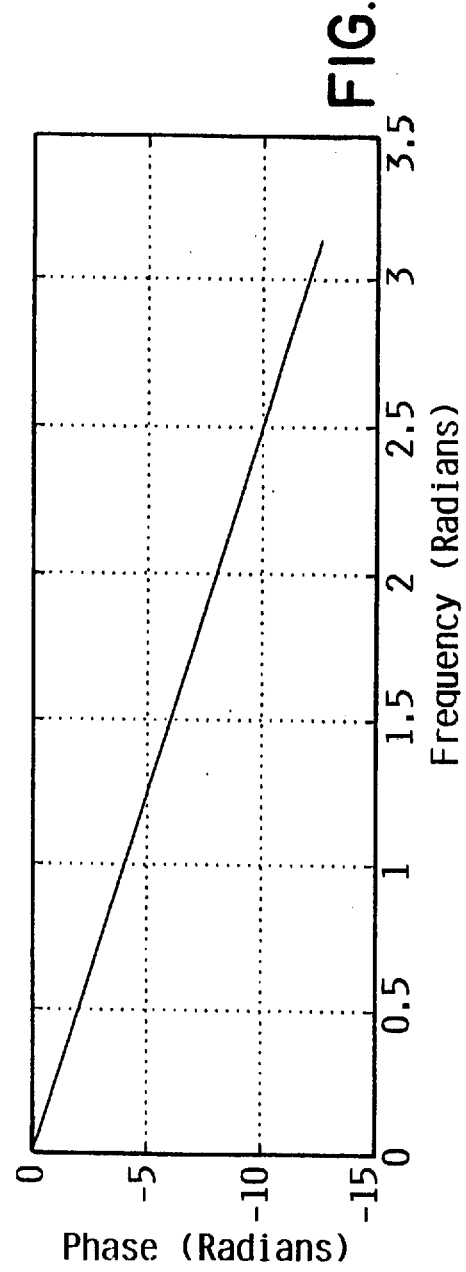

In particular, it can be seen in FIG. 19(*b*) that the 9-tap filter exhibits perfect linear phase response over the frequency range of interest. The effectiveness of the 9-tap FIR filter in eliminating the baseline shift or modulation of the readback signal is demonstrated in FIG. 18. FIG. 18(*a*) shows a readback signal demonstrating an unstable or time-varying baseline. In FIG. 18(*b*), the modulating baseline of the readback signal apparent in FIG. 18(*a*) has been eliminated after passing the distorted readback signal through an appropriately programmed 9-tap FIR filter. The tap weights for the 9-tap filter used to restore the baseline of the readback signal was defined to include tap weights of:

$$B(i)=(1/9)*(-1, -1, -1, -1, 8, -1, -1, -1, -1),$$

or $$B(i)=(-0.111, -0.111, -0.111, -0.111, 0.889, -0.111, -0.111, -0.111, -0.111)$$

The waveform shown in FIG. 18(*c*) was produced by passing the modulated readback signal shown in FIG. 18(*a*) through a conventional highpass Butterworth filter, which is a single-pole highpass filter. It can be seen that the undesirable modulating baseline of the readback signal is not significantly reduced in magnitude after passing the readback signal through a conventional highpass filter.

As previously indicated, the magnitude and phase characteristics of the 9-tap FIR filter used to restore the baseline of the readback signal as shown in FIG. 18(*b*) are respectively shown in FIGS. 19(*a*) and 19(*b*). It can be seen in FIG. 19(*a*) that some degree of ripple may occur in the passband of the filter which may be eliminated by applying a window function to the tap weights of the 9-tap FIR filter. By way of example, a Hamming window can be applied to the tap weights of the 9-tap FIR filter to produce a windowed restore filter having the following tap weights:

$$b(i)=(-0.0089, -0.0239, -0.06, -0.0961, 0.8889, -0.0961, -0.06, -0.0239, -0.0089)$$

The output of the 9-tap windowed FIR filter having the above-listed tap weights results in the elimination of the ripple as shown in FIG. 20(*a*). As further shown in FIG. 20(*b*), the windowed 9-tap FIR filter retains its perfect linear phase response. It is noted that applying a window function, such as a Hamming window, to the tap weights of the programmable FIR filter 488 allows for a non-zero DC gain and some increase in low frequency response.

Turning now to FIGS. 23–29, there is illustrated another embodiment of a signal separation/restoration module 476. In the design of an AE module 202 as illustrated in FIG. 13, it is often desirable to include a highpass filter in conjunction with a preamplifier for purposes of rejecting the relatively low frequency signal content of the composite readback signal produced by the MR head 80. The highpass filter of the AE module 202 distorts both in amplitude and phase the thermal signal component of the composite readback signal. The magnitude of the thermal signal distortion due to the highpass filter varies in severity depending on the frequency and phase response of the particular highpass filter employed.

By way of example, a highpass filter suitable for use in an AE module 202 may have a cutoff frequency of approximately 500 KHz and exhibit non-linear phase behavior. The frequencies associated with head-to-disk spacing changes, however, typically range below 200 KHz. Moreover, the thermal signal of a readback signal typically has a frequency ranging between 10 KHz to approximately 100 KHz. It can be appreciated that a highpass filter having a cutoff frequency of approximately 500 KHz will significantly distort the amplitude and phase of the thermal signal component of the readback signal. The magnetic signal component of the readback signal, however, remains unaffected by the highpass filter since the frequency range for the magnetic signal is generally some 20 to 40 times that of the highpass filter cutoff frequency.

Figure 23A:
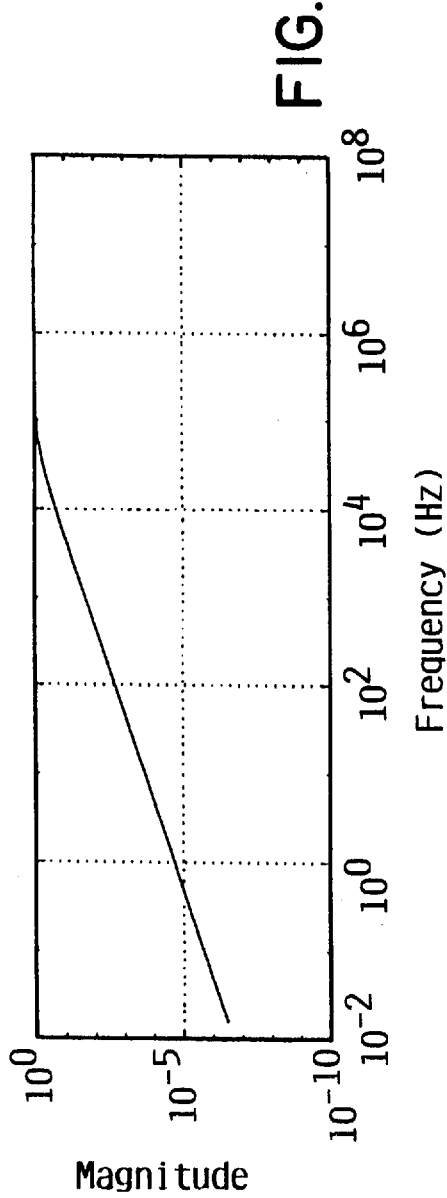
FIGS. 23(a) and 23(b) are a showing of the magnitude and phase response of the highpass filtering behavior of a typical AE module.
Figure 23B:
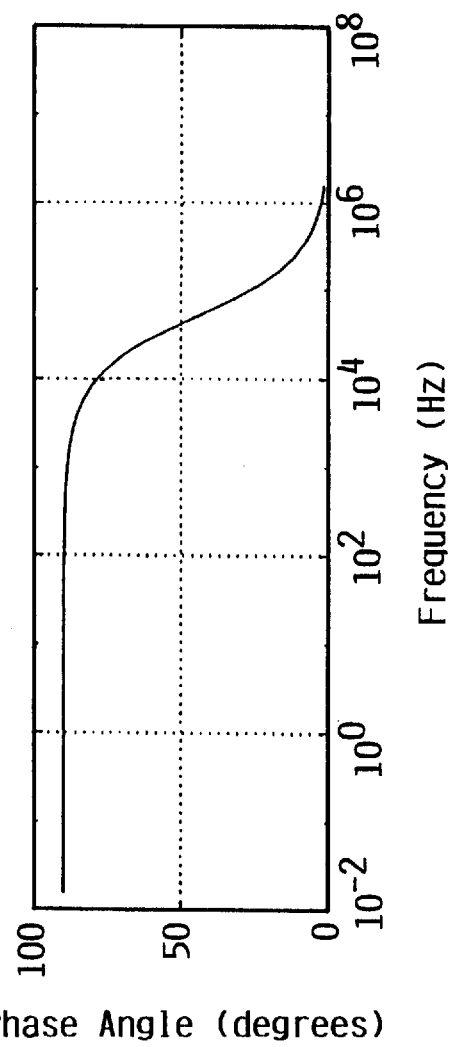
Figure 24:
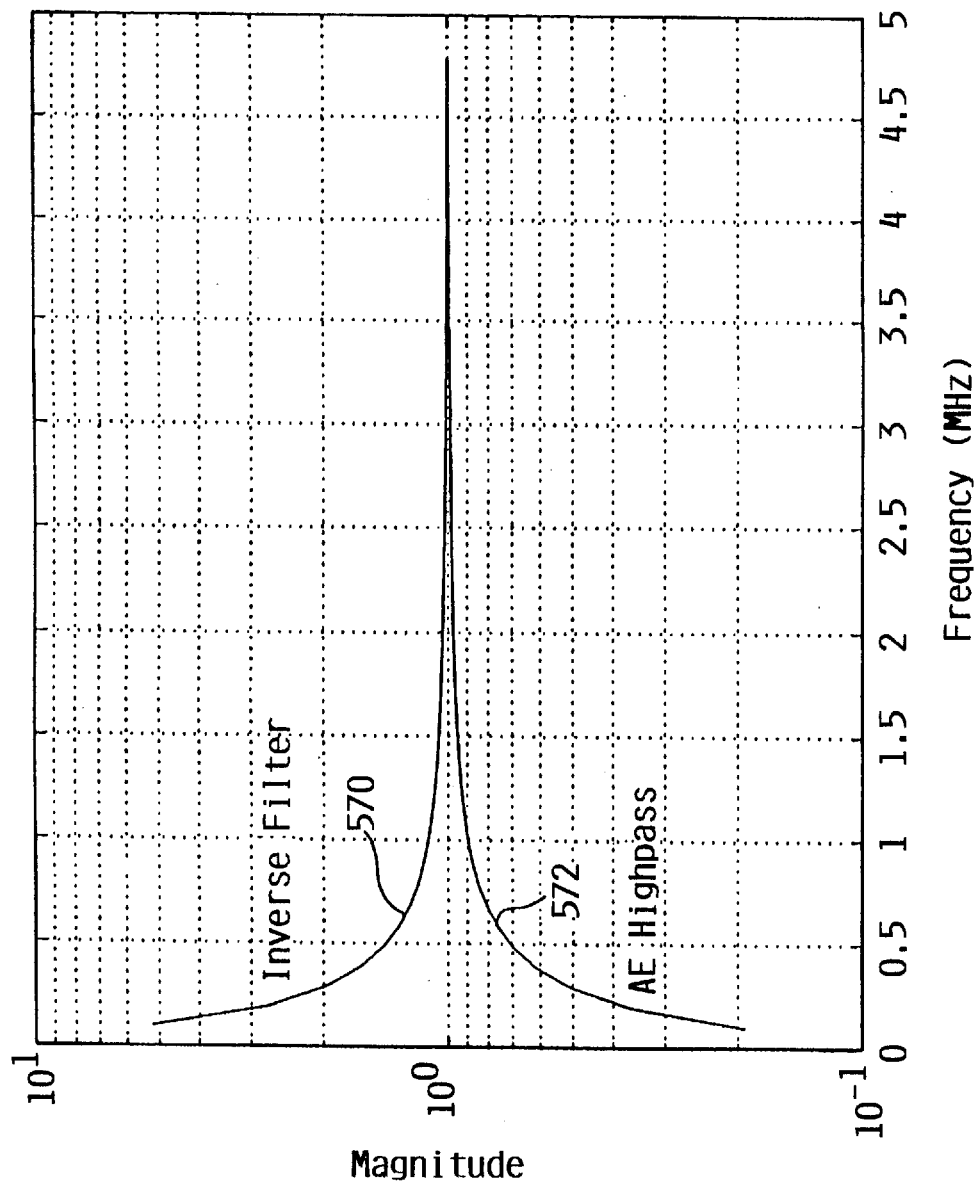
FIGS. 24 and 25 respectively show a comparison of the magnitude and phase response of the highpass filtering behavior of a typical AE module and an inverse filter having a transfer function inverse to that of the effective highpass filter of the AE module.
Figure 25:
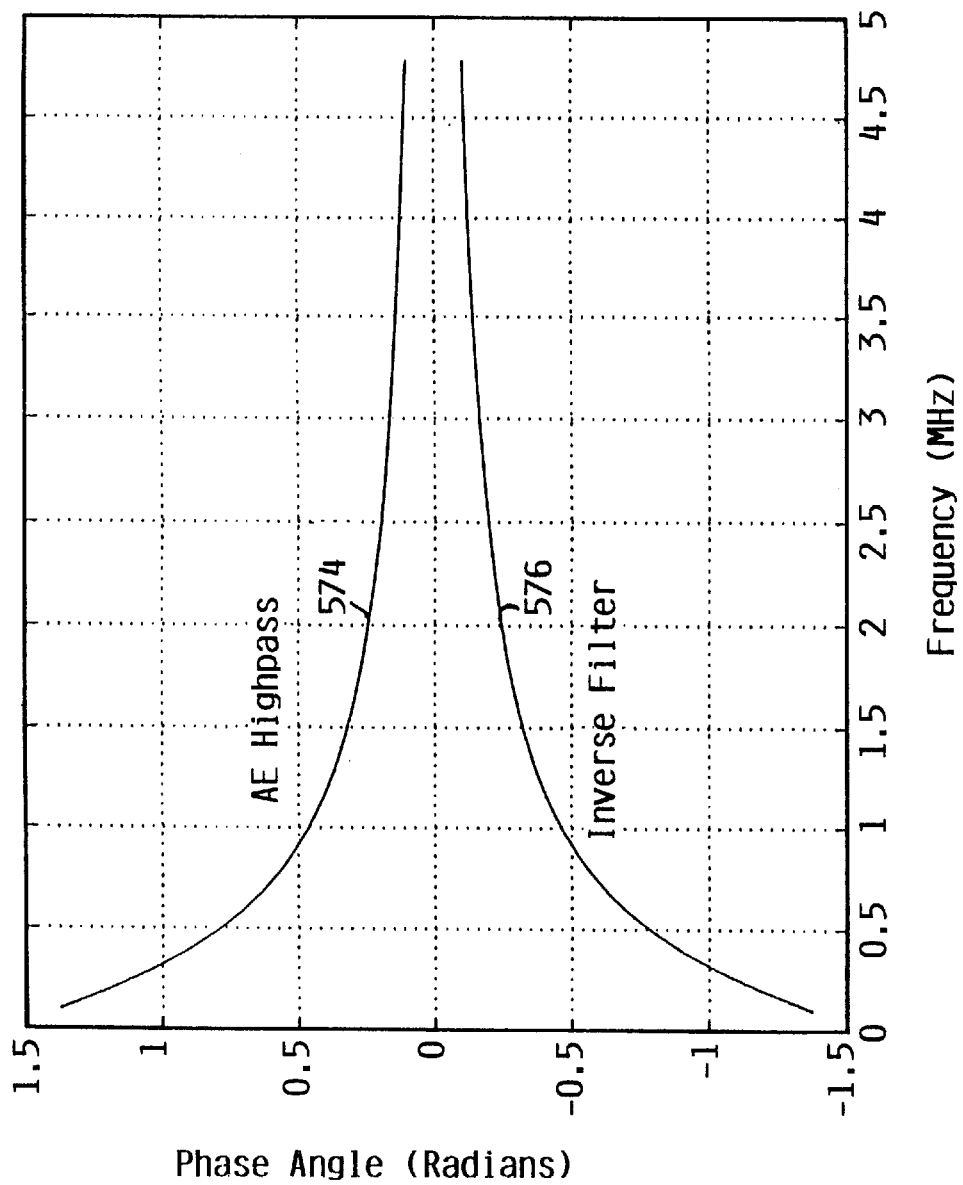

In FIGS. 23(a) and 23(b), there is respectively illustrated graphs showing the magnitude and phase response of the highpass filtering behavior of a typical AE module 202. The highpass filter has a cutoff frequency of approximately 500 KHz. The transfer function for the highpass filter having a single pole at 500 KHz and the magnitude and phase response illustrated in FIG. 23 can be defined as:

$$H = \frac{b_h(1) + b_h(2) \cdot z^{-1}}{1 + a_h(2) \cdot z^{-1}} \quad [1]$$

where:

$b_h(1)$=0.9876

$b_h(2)$=−0.9876

$a_h(2)$=−0.9752

The distortion to the amplitude and phase of a thermal signal introduced by the highpass filter of the AE module 202 is effectively eliminated by use of an inverse filter having a transfer function inverse to that of the highpass filter. Passing the readback signal output from the AE module 202 through the inverse filter restores the thermal signal to its original form, both in amplitude and phase. For example, the transfer function of an inverse filter for conditioning a readback signal passed through a highpass filter having the above-described transfer function of equation [1] is:

$$H^{-1} = \frac{1 + a_h(2) \cdot z^{-1}}{b_h(1) + b_h(2) \cdot z^{-1}} \quad [2]$$

The magnitude and phase response for the highpass filter of the AE module 202 and the inverse filter described above are respectively plotted in FIGS. 24 and 25. In particular, the magnitude response of the inverse filter and the highpass filter of the AE module 202 is respectively shown as curves 570 and 572 in FIG. 24. The phase response of the inverse filter and highpass filter is respectively shown as curves 576 and 574.

In one embodiment, an infinite impulse response (IIR) filter is programmed to respond as an inverse filter for purposes of restoring the thermal signal content of a highpass filtered readback signal. Although an analog filter can be employed in an alternative embodiment, an IIR filter provides a number of advantages well-suited for use as an inverse filter for purposes of restoring the amplitude and phase of a thermal signal distorted by the highpass filter behavior of the AE module 202.

Figure 26:
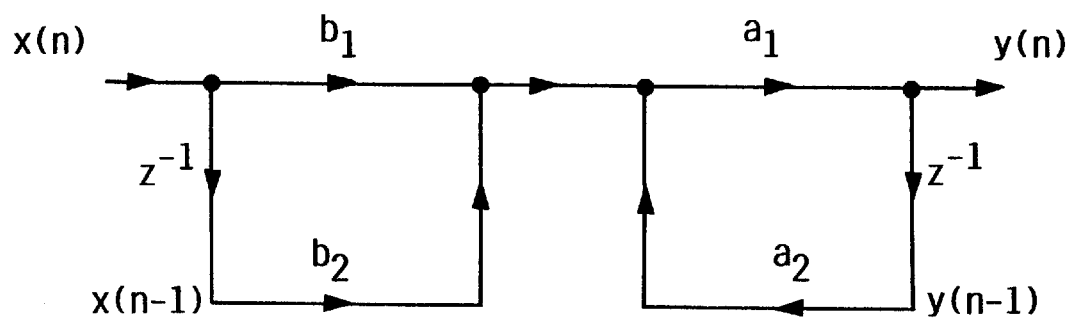
FIG. 26 is a signal flow diagram representative of the inverse filter of FIGS. 24 and 25.

The signal flow diagram illustrated in FIG. 26 is representative of a first order IIR filter configured as an inverse filter. The coefficients associated with the signal flow graph of FIG. 26 for a first order IIR inverse filter having a transfer function given by quation [2] above are:

$a_1$=0.9876

$a_2$=−0.9876

$b_1$=0.1

$b_2$=−0.9752

Figure 28A:
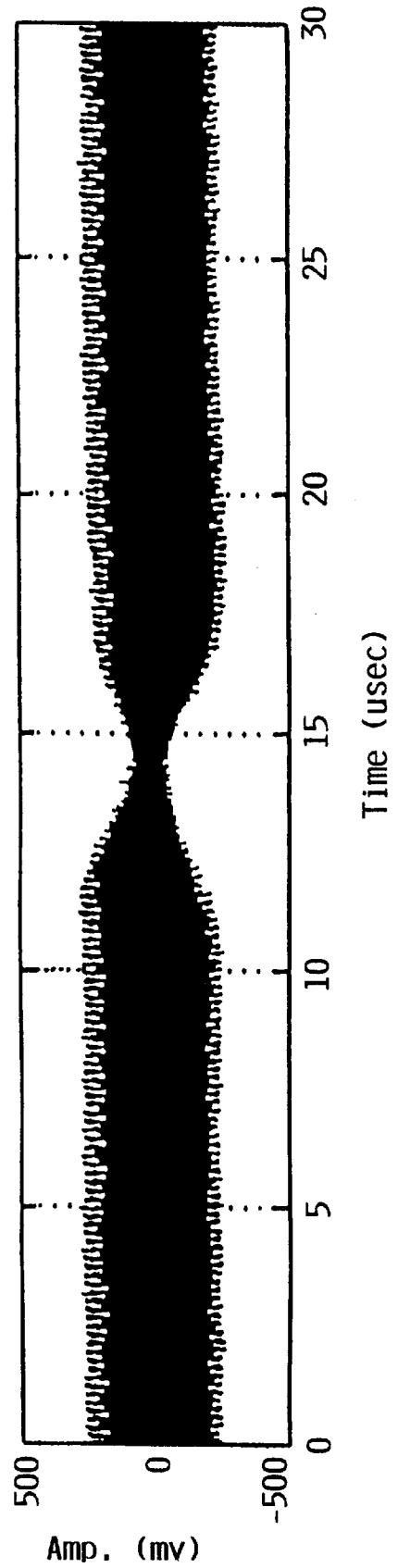
FIGS. 28(a)–28(c) show three waveforms produced at different processing points within the signal separation/restoration module of FIG. 27.
Figure 28B:
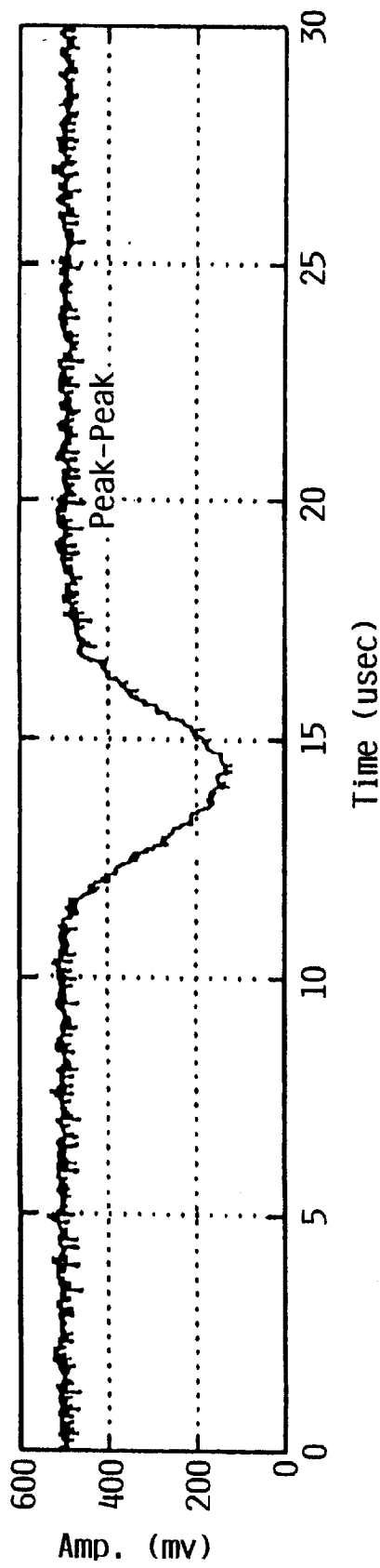
Figure 28C:
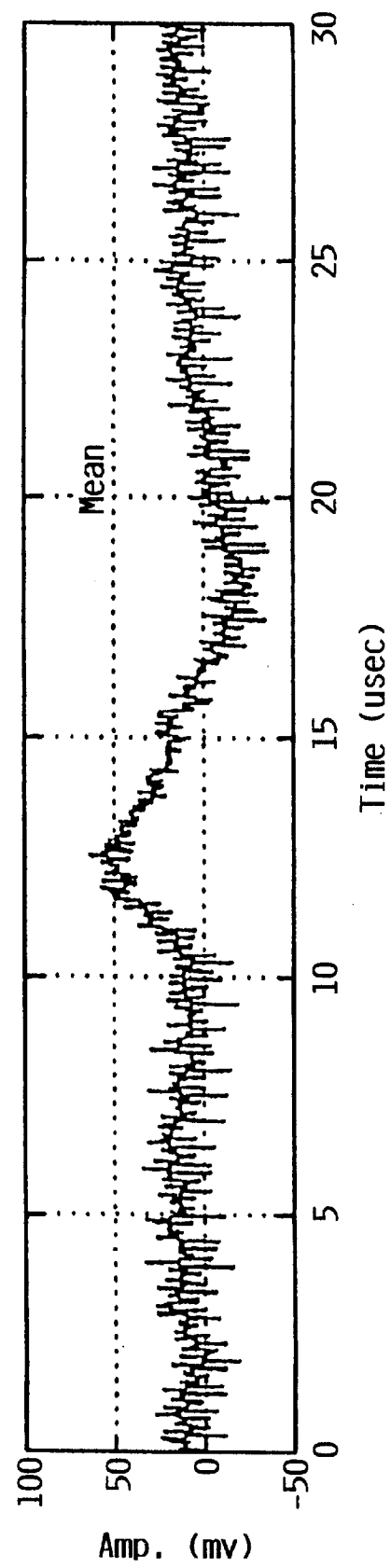

In FIG. 28, there is illustrated three waveforms that demonstrate the effectiveness of the inverse filter for restoring the original amplitude and phase of the thermal signal component of a readback signal that has been passed through a highpass filter. In FIG. 28(a), there is shown a readback signal detected from a pit in a data storage disk surface. The readback signal shown in FIG. 28(a) was detected from a track written at a 20 MHz write frequency. The readback signal was sampled at 100 MHz with 8-bit resolution. The graph shown in FIG. 28(b) represents the calculated peak-to-peak magnitude of the readback signal of FIG. 28(a). The signal shown in FIG. 28(b), accordingly, represents the magnetic spacing signal 560 which clearly shows a loss of magnetic signal due to the MR read element passing over the pit. FIG. 28(c) illustrates the thermal signal component of the readback signal after having been passed through the highpass filter 550 of the AE module 202. It can be seen by comparing the waveforms of FIGS. 28(b) and 28(c) that the magnetic spacing information and thermal spacing information do not correspond closely with one another because of the distortion to the thermal signal component caused by the highpass filter 550, which has essentially differentiated the thermal signal. For more details on designing, implementing, and programming an IIR filter for use as an inverse filter, reference is made to E. C. Ifeachor, B. W. Jervis, "Digital Signal Processing" (Addison-Wesley Publishing Company, Inc. 1993).

Figure 29:
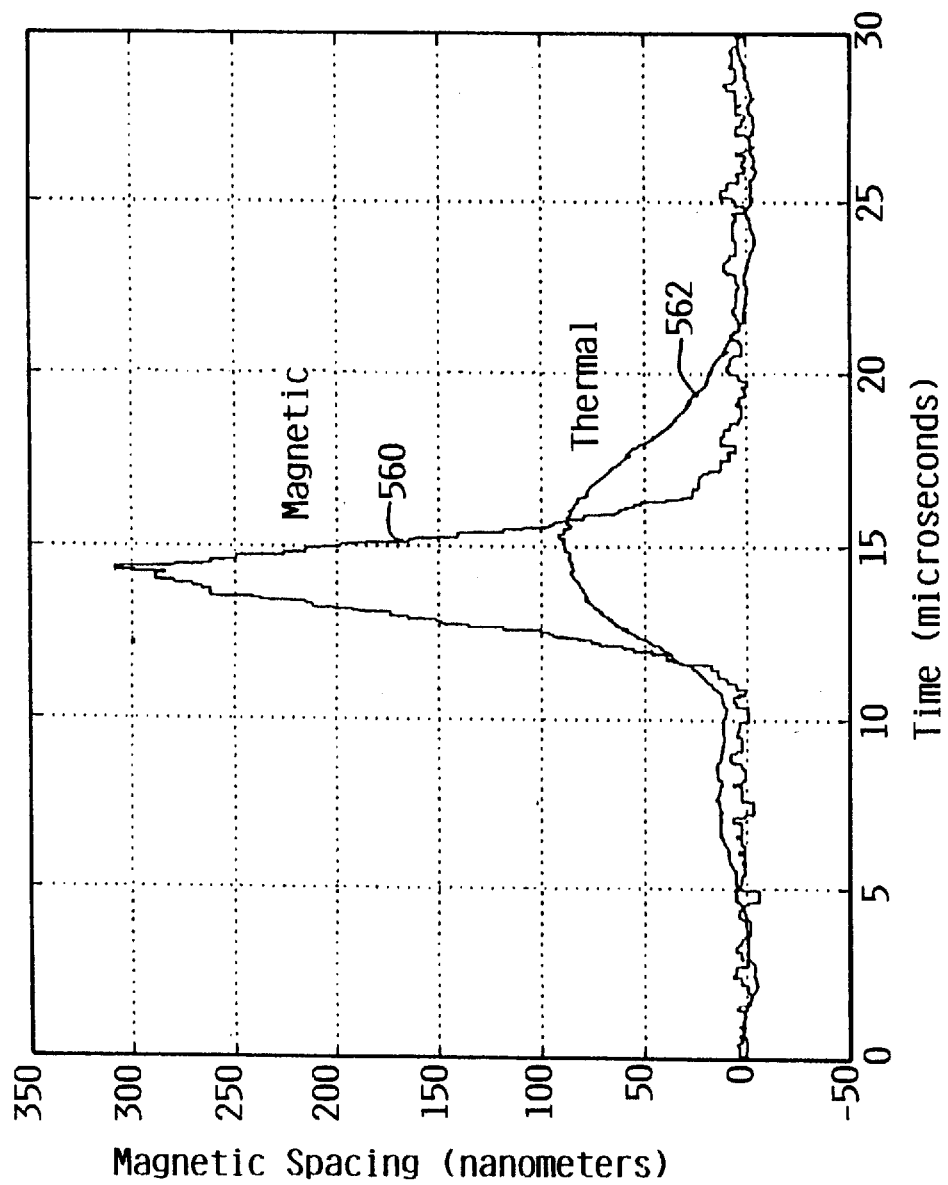
FIG. 29 is a comparative showing of a restored magnetic signal and thermal signal indicating the presence of a bump on a disk surface.

In FIG. 29, the thermal spacing signal 562 processed by the inverse filter 556 and mean filter 558 is illustrated together with the magnetic spacing signal 560 passed through the digital filter 552 and log device 554. It is noted that the linearized magnetic spacing signal 560 is typically calculated by taking the logarithm of the peak-to-peak signal and then multiplied by the known sensitivity of the output voltage change to magnetic spacing change in accordance with the well-known Wallace equation. It can be seen in FIG. 29 that except for a difference in signal height and a slightly longer time constant associated with the thermal spacing signal 562, a magnetic spacing signal 560 and thermal spacing signal 562 describe a disk surface pit. Thus, the integrating effect that the inverse filter 556 on the distorted thermal signal shown in FIG. 28(c) provides for a correct thermal spacing signal 562 to be produced.

Figure 27:
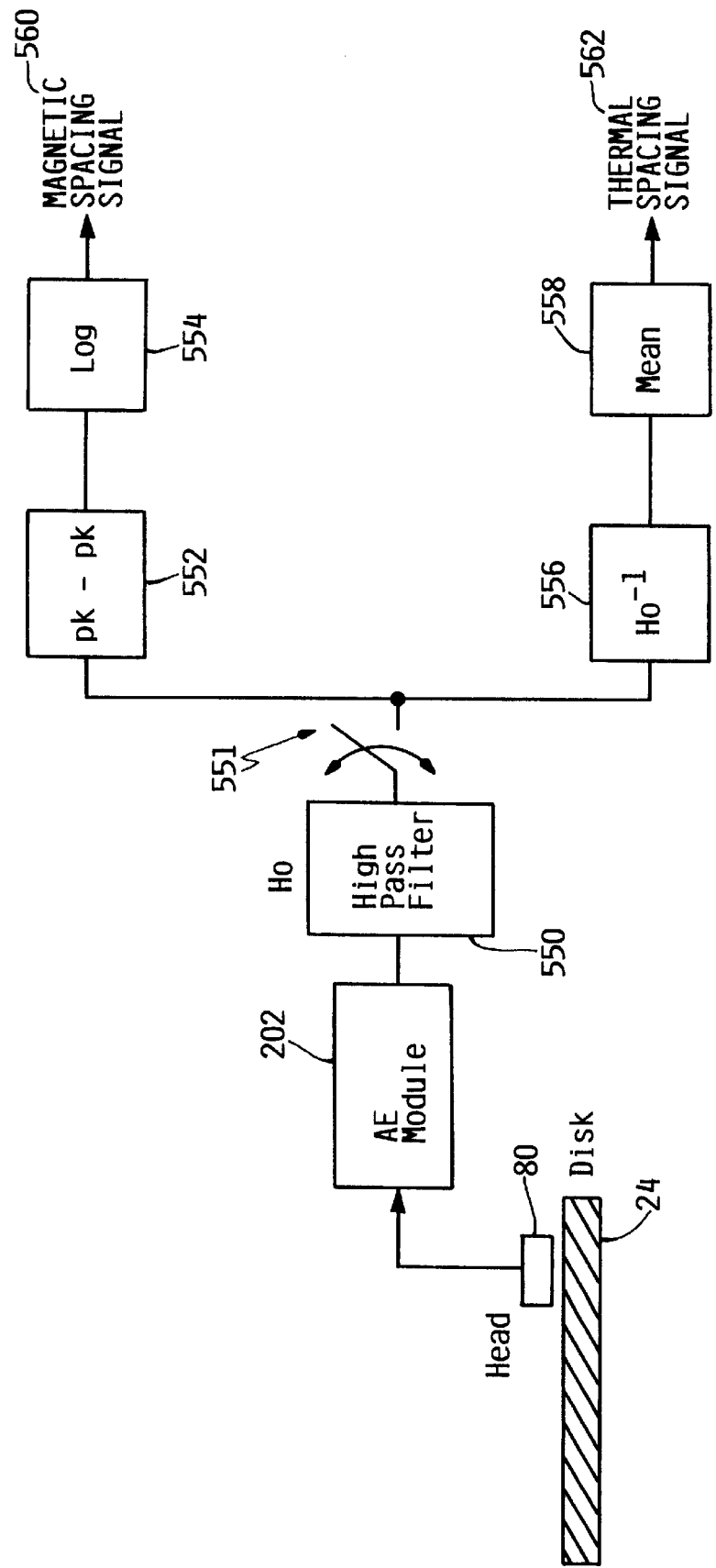
FIG. 27 is a block diagram of another embodiment of a signal separation/restoration module employing an infinite impulse response (IIR) filter.

Referring to FIG. 27, there is shown in block diagram form a system for processing a readback signal to obtain magnetic and thermal head-to-disk spacing information. A readback signal is detected from the disk surface 24 by the MR head 80. It is assumed that the readback signal is a composite signal containing both magnetic and thermal signal components. The readback signal detected by the MR head 80 is communicated to the AE module 202 and then to a highpass filter 550. The highpass filter 550 is shown as a component external to the AE module 202. In general practice, however, the highpass filter 550 is incorporated into the AE module 202. The transfer function of the highpass filter is denoted as $H_o$.

The output signal from the highpass filter 550 is sampled by an analog-to-digital converter 551 to create digitized samples of the highpass filtered readback signal. The digitized readback signal is then communicated to the inverse filter 556 which corrects for the distortion introduced by the highpass filter 150 of the AE module 202. The transfer function of the inverse filter 556 is denoted as $H_o^{-1}$. The mean of the signal passed through the inverse filter 556 is obtained by digital filtering using a mean filter 558 to produce a thermal signal which is linearly related to the head-to-disk spacing.

The readback signal provided at the output of the analog-to-digital converter 551 may also be communicated to a digital filter 552, such as a FIR filter, that extracts the peak-to-peak amplitude of the readback signal so as to extract the magnetic signal component from the readback signal. The logarithm of the magnetic signal is obtained by passing the magnetic signal through the log device 554, which produces a magnetic signal that is linearly related to the head-to-disk spacing. Having extracted both the magnetic and thermal spacing signals 560 and 562, respectively, the thermal signal can be calibrated since the magnetic calibration is known and only depends on the recorded wavelength of the signal. It is important to note that both the magnetic and thermal spacing signals 560 and 562 are linearly proportional to the head-to-disk spacing (y).

Figure 21:
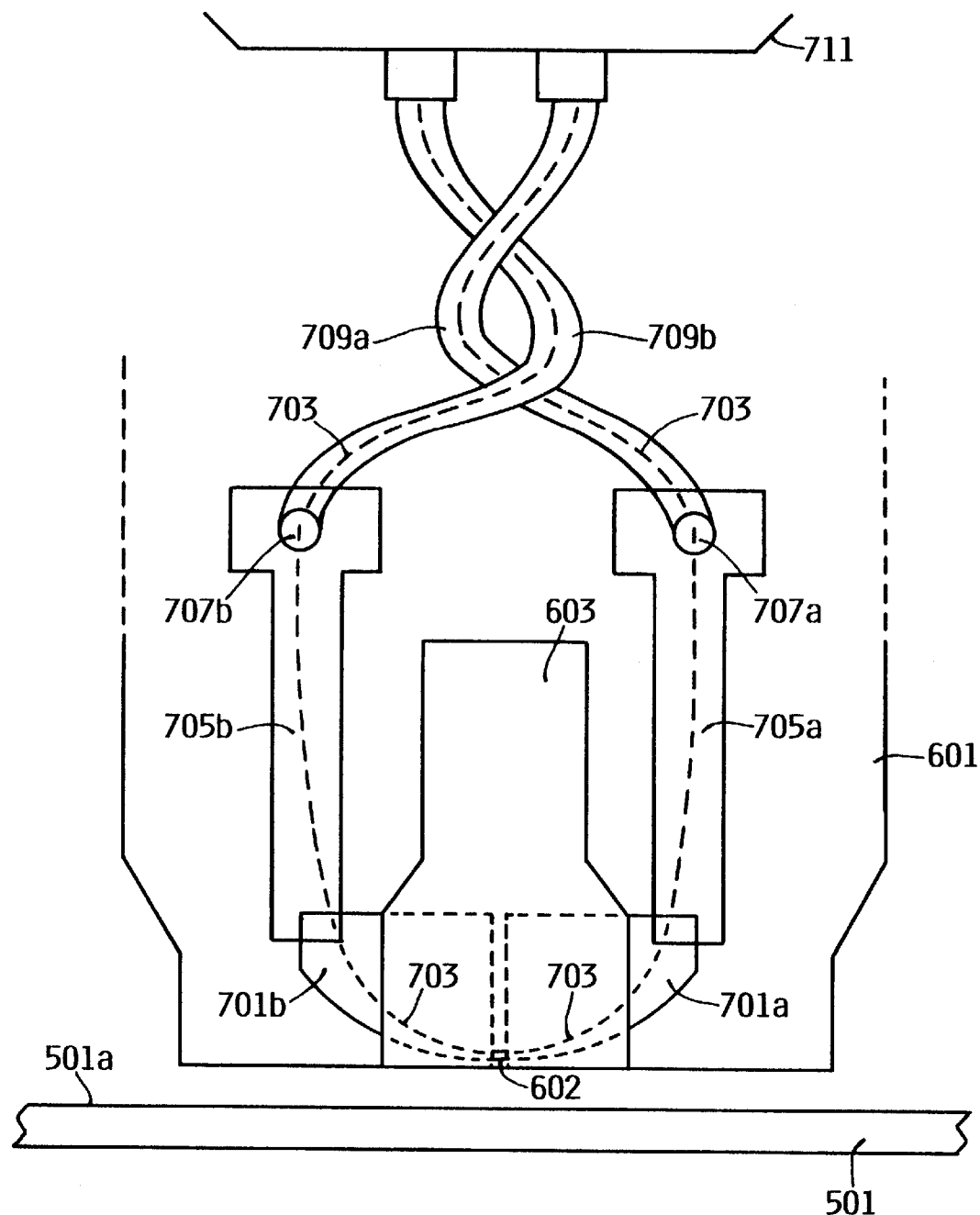
FIGS. 21 and 22 is an illustration of a conventional MR head.
Figure 22:
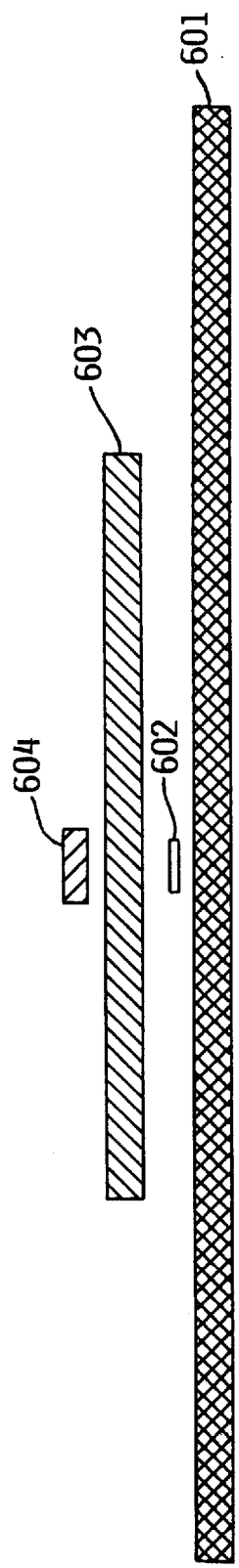

In order to more fully appreciate the various aspects of the present invention, a brief discussion of a conventional MR head is provided. The general layout of the principle elements in a typical merged MR head 600 is illustrated in FIGS. 21 and 22. The illustrations are not drawn to scale, but rather are provided to illustrate the relative orientation of the various MR head elements. The MR head includes a pair of shields 601 and 603. An MR element 602 is located between the shields 601 and 603. The MR element 602 operates as a read element of the MR head 600.

Element 603 in conjunction with element 604 form a thin film magnetic head functioning as a write element for the MR head 600. Elements 603 and 604 operate respectively as first and second magnetic poles of the thin film write element. The dual function of element 603 (i.e., acting as a first pole of the write element and as a second shield) results in the merged nature of the MR head 600. Insulation layers (not shown for purposes of clarity), such as glass, are typically formed between the various elements of the MR head 600.

As further depicted in FIGS. 21 and 22, the first shield 601, MR element 602, and second shield 603 extend upward from the surface 501A of a disk 501 in respective vertical planes. The second pole 604 is not shown in FIG. 21 for purposes of clarity. The planes of the elements are illustrated parallel running in the direction of the plane of the page. In the illustrations, the plane of the first pole/second shield 603 is closest, followed by the MR element 602, with the first shield 601 being furthest away. Also depicted, are the negative and positive MR leads 701A and 701B, respectively. These leads are formed in a plane between the first shield 601 and the first pole/second shield 603. The leads 701A and 701B are electrically coupled to the MR element 602 in a known manner and operate in the normal fashion. Connected to leads 701A and 701B, are extended leads 705A and 705B, respectively. The extended leads 705A and 705B have connection points 707A and 707B which are respectively connected to lead wires 709A and 709B which, in turn, are connected to a preamplifier module 711.

The physical phenomena that generates the thermal voltage response $V_{TH}$ across the MR head element 602 is that as the instantaneous head-to-disk spacing increases, there is more air space between the head 600 and the disk surface 101A causing the MR element 602 to heat up. This heating cause the MR head 600 resistance to increase due to the positive temperature coefficient of the material constituting the MR element 602. For example, permalloy has temperature coefficient of $+3\times10^{-3}/°$ C. as mentioned previously. At a constant bias current, the voltage $V_{TH}$ across the MR element 602 resistance will increase. If the MR element 602 comes in close proximity to the disk surface 501A, more heat transfer will occur between the MR element 602 and the disk surface 501A causing cooling of the MR element 602. The resulting lowering of the MR head 600 resistance will lower the voltage $V_{TH}$ across the MR element 602 at a constant bias current.

It will, of course, be understood that various modifications and additions can be made to the embodiments discussed hereinabove without departing from the scope or spirit of the present invention. For example, the novel servo positioning method and apparatus may be employed in systems employing optical data disks, or disks having spiralled or other non-concentric track configurations. Accordingly, the scope of the present invention should not be limited to the particular embodiments discussed above, but should be defined only by full and fair scope of the claims set forth below.

What is claimed is:

1. A method of calibrating a magnetoresistive (MR) head of a storage system having at least one disk and at least one MR head, the method comprising the steps of:

providing said disk with a calibration zone having surface profile variations;

moving an MR head to said calibration zone;

inducing thermal signals in said MR head with said surface profile variations; and measuring MR head and disk characteristics using said thermal signals.

2. A method as recited in claim 1, wherein said surface profile variations include a first frequency pattern and a second frequency pattern, said calibration method further comprising the steps of:

inducing thermal frequency signals in said MR head with said first and second frequency patterns;

determining MR head thermal thresholds using said thermal frequency signals.

3. A method as recited in claim 2, further comprising the step of storing said thermal thresholds in a random access memory.

4. A method as recited in claim 3, wherein said measuring step measuring MR head axial offset and disk eccentricity.

5. A method as recited in claim 4, wherein said measuring step comprises the step of averaging absolute measurements of disk eccentricity over one revolution of said disk.

6. A method as recited in claim 1, which further comprises the steps of:

repeating the steps recited in claim 1 for each MR head in said storage system;

setting a reference one of said MR heads to physical track zero for cylinder zero of said storage system; and mapping said MR heads other than said reference MR head to physical tracks based on said reference MR head axial offset.

7. A method as recited in claim 6, wherein said reference MR head comprises said MR head with the largest MR head axial offset.

\* \* \* \* \*